US008287906B2

(12) United States Patent
Kurisawa et al.

(10) Patent No.: US 8,287,906 B2
(45) Date of Patent: Oct. 16, 2012

(54) FORMATION OF HYDROGEL IN THE PRESENCE OF PEROXIDASE AND LOW CONCENTRATION OF HYDROGEN PEROXIDE

(75) Inventors: Motoichi Kurisawa, Singapore (SG); Li Shan Wang, Singapore (SG); Joo Eun Chung, Singapore (SG); Fan Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 319 days.

(21) Appl. No.: 12/545,004

(22) Filed: Aug. 20, 2009

(65) Prior Publication Data
US 2010/0074956 A1     Mar. 25, 2010

Related U.S. Application Data

(63) Continuation-in-part of application No. 12/436,757, filed on May 6, 2009, now abandoned, which is a continuation-in-part of application No. PCT/SG2008/000204, filed on Jun. 5, 2008.

(60) Provisional application No. 61/071,559, filed on May 6, 2008.

(51) Int. Cl.
*A61K 9/10* (2006.01)
*C12Q 1/28* (2006.01)
*C12P 1/00* (2006.01)
*C12N 5/02* (2006.01)

(52) U.S. Cl. ............. 424/486; 435/28; 435/41; 435/396

(58) Field of Classification Search ........................ None
See application file for complete search history.

(56) References Cited

U.S. PATENT DOCUMENTS

| 6,679,918 B1 | 1/2004 | Benedict et al. |
| 2004/0147673 A1 | 7/2004 | Calabro et al. |
| 2006/0084759 A1* | 4/2006 | Calabro et al. ............... 525/54.1 |

FOREIGN PATENT DOCUMENTS

| DE | 19963251 | 6/2001 |
| WO | 2001049327 | 7/2001 |
| WO | 2006124000 A1 | 11/2006 |
| WO | 2007095175 A2 | 8/2007 |
| WO | 2007097710 A1 | 8/2007 |
| WO | WO 2007097710 A1 * | 8/2007 |

OTHER PUBLICATIONS

Kurisawa, Chem. Commun., 2005.*
Lee, Soft Matter, 4, Feb. 29, 2008.*
Kurisawa et al., "Injectable biodegradable hydrogels composed of hyaluronic acid-tyramine conjugates for drug delivery and tissue engineering," Chemical Communications, 2005, pp. 4312-4314.
F. Lee et al., "An injectable enzymatically crosslinked hyaluronic acid-tyramine hydrogel system with independent tuning of mechanical strength and gelation rate," Soft Matter, 2008, pp. 880-887, vol. 4.
Jin et al., "Enzyme-mediated fast in situ formation of hydrogels from dextran-tyramine conjugates", Biomaterials, 2007, pp. 2791-2800, vol. 28, issue 18.
Engler A. J. et al., "Matrix elasticity directs stem cell lineage specification," Cell, 2006, pp. 677-689, vol. 126.
Sakai et al., "Both ionically and enzymatically crosslinkable alginate-tyramine conjugate as materials for cell encapsulation," Journal of Biomedical Materials Research Part A, 2008, pp. 345-351, vol. 85A.
Sakai et al., "Synthesis and characterization of both ionically and enzymatically cross-linkable alginate", Acta Biomaterialia, 2007, pp. 495-501, vol. 3, issue 4.
Australian Patent Office, "Written Opinion of the International Searching Authority", mailed Aug. 20, 2008, in PCT Application No. PCT/SG2008/000204.
Australian Patent Office, "Written Opinion of the International Preliminary Examining Authority", mailed Jan. 19, 2009, in PCT Application No. PCT/SG2008/000204.
Australian Patent Office, "Written Opinion of the International Preliminary Examining Authority", mailed Apr. 3, 2009, in PCT Application No. PCT/SG2008/000204.
Australian Patent Office, "Written Opinion of the International Preliminary Examining Authority", mailed Jun. 23, 2009, in PCT Application No. PCT/SG2008/000204.
Australia Patent Office, "International Preliminary Report on Patentability", mailed Sep. 3, 2009, in PCT Application No. PCT/SG2008/000204.
Saito et al., "Experimental studies on a new bioactive bone cement: hydroxyapatite composite resin", 1994, Biomaterials, vol. 15, No. 2, pp. 156-160.
Deb, S. et al., "Development of high-velocity, two-paste bioactive bone cements", 2005, Biomaterials, vol. 26, pp. 3713-3718.
International Search Report and Written Opinion, mailed Apr. 24, 2006, in PCT Application No. PCT/SG2006/000039. International Preliminary Report on Patentability, dated Sep. 2, 2008, in PCT Application No. PCT/SG2006/000039.
United States Patent and Trademark Office, "Office Action", dated Jun. 1, 2011, in U.S. Appl. No. 12/280,777.
United States Patent and Trademark Office, "Office Action", dated Sep. 1, 2011, in U.S. Appl. No. 12/280,777.
United States Patent and Trademark Office, "Office Action", dated Jun. 1, 2011, in U.S. Appl. No. 12/330,436.
United States Patent and Trademark Office, "Office Action", dated Sep. 9, 2011, in U.S. Appl. No. 12/330,436.

* cited by examiner

*Primary Examiner* — Robert A Wax
*Assistant Examiner* — William Craigo
(74) *Attorney, Agent, or Firm* — Klarquist Sparkman, LLP

(57) ABSTRACT

In a process of forming a hydrogel from a mixture comprising hydrogen peroxide ($H_2O_2$), horseradish peroxidase (HRP), and a polymer comprising a crosslinkable phenol group, the gelation rate in the solution and the crosslinking density in the hydrogel can be independently adjusted or controlled by selection of the molarity of $H_2O_2$ and concentration of HRP in the solution when the molarity of $H_2O_2$ is limited to be within a range and the concentration of HRP is limited to be above a threshold. A method for determining the range and threshold is disclosed. The hydrogel may be used to grow cells, in which case, the molarity of $H_2O_2$ may be selected to affect the differentiation or growth rate of the cells in the hydrogel.

38 Claims, 10 Drawing Sheets

FORMATION OF HYDROGEL IN THE PRESENCE OF PEROXIDASE AND LOW CONCENTRATION OF HYDROGEN PEROXIDE

CROSS-REFERENCE TO RELATED APPLICATIONS

This is a continuation-in-part of application Ser. No. 12/436,757, filed May 6, 2009 now abandoned, which is a continuation-in-part of International Application No. PCT/SG2008/000204, filed Jun. 5, 2008, the entire contents of each of which are incorporated herein by reference.

This is a continuation-in-part of application Ser. No. 12/436,757, filed May 6, 2009, which claims the benefit of U.S. Provisional Application No. 61/071,559, filed May 6, 2008, the entire contents of each of which are incorporated herein by reference.

FIELD OF THE INVENTION

The present invention relates to hydrogel formation, particularly to formation of hydrogels in the presence of peroxidase and hydrogen peroxide.

BACKGROUND OF THE INVENTION

Phenol-containing hydrogels, such as hyaluronic acid-tyramine (HA-Tyr) hydrogels, are useful in many applications, including drug or protein delivery and tissue regeneration. Such hydrogels can be formed from a phenol-containing polymer, such as a HA-Tyr conjugate, in the presence of horseradish peroxidase (HRP) and hydrogen peroxide ($H_2O_2$) as catalysts. In conventional techniques, the gelation rate and the crosslinking density in the hydrogel can be adjusted by changing the concentration of HRP or $H_2O_2$ in the precursor solution. Such a change typically affects both the gelation rate and crosslinking density.

Certain types of gelatin-based hydrogels have been used as drug carriers or tissue engineering scaffolds. These hydrogels are either chemically crosslinked by covalent bonding, or physically crosslinked by hydrophobic interaction or hydrogen bonding. Typically, chemically crosslinked known gelatin-based hydrogels are crosslinked with cross-linkers such as glutaraldehyde, carbodiimide, or diphenylphosphoryl azide, which can induce cytotoxicity or reduce bioactivity of the active ingredient encapsulated in the hydrogels. Both cytotoxicity and reduced bioactivity limit the application of such hydrogels. Physical crosslinking can avoid inducing cytotoxicity and reduced bioactivity. However, existing physically crosslinked gelatin hydrogels have reduced in vivo stability due to internal mechanical stress and molecular interaction between the hydrogel and the physiological molecules. It is also difficult to adjust the mechanical properties of the physically crosslinked gelatin-based hydrogel. The mechanical properties of the known chemically crosslinked gelatin-based hydrogels can be changed by varying the concentrations of the reagents and catalysts in the production process. However, such adjustments can also affect the formation rate of the hydrogel and are thus constrained.

SUMMARY OF THE INVENTION

In accordance with an aspect of the present invention, there is provided a method of determining a range for hydrogen peroxide ($H_2O_2$) molarity and a threshold for horseradish peroxidase (HRP) concentration, comprising forming a plurality of hydrogels from a plurality of solutions, each one of the solutions comprising a polymer comprising a crosslinkable phenol group, HRP, and $H_2O_2$, the solutions having the same concentration of the polymer, some of the solutions having the same $H_2O_2$ molarity but different HRP concentrations and some of the solutions having the same HRP concentration but different $H_2O_2$ molarities; measuring a first metric indicative of a gelation rate in each one of the solutions during the forming and a second metric indicative of a crosslinking density in each one of the hydrogels; determining the range for $H_2O_2$ molarity and the threshold for HRP concentration, by requiring that (1) the first metric is substantially constant for solutions that have the same HRP concentration above the threshold but have different $H_2O_2$ molarities each within the range, and (2) the second metric is substantially constant for solutions that have the same $H_2O_2$ molarity within the range but have different HRP concentrations each above the threshold. The first metric may be time required to reach gel point and the second metric may be storage modulus.

In accordance with another aspect of the present invention, there is provided a method of forming a hydrogel, comprising selecting an amount of horseradish peroxidase (HRP) and an amount of hydrogen peroxide ($H_2O_2$); and mixing a polymer comprising a crosslinkable phenol group, the amount of HRP and the amount of $H_2O_2$ in a solution, to crosslink the polymer to form the hydrogel, wherein the amount of HRP and the amount of $H_2O_2$ are selected to independently control a gelation rate in the solution and a crosslinking density in the hydrogel, with a constraint that the $H_2O_2$ molarity in the solution is within a pre-determined range and the HRP concentration in the solution is above a pre-determined threshold, the pre-determined range and threshold having been determined on the basis that, if the $H_2O_2$ molarity in the solution is limited to be within the range and the HRP concentration in the solution is limited to be above the threshold, the gelation rate in the solution would be substantially unaffected by variation in the selection of the $H_2O_2$ molarity within the range, and the crosslinking density in the hydrogel would be substantially unaffected by variation in the selection of the HRP concentration above the threshold. The pre-determined range and threshold may be determined according to a method described herein. The $H_2O_2$ molarity may be selected so that the hydrogel formed from the solution has a pre-selected storage modulus. The polymer may comprise a conjugate of hyaluronic acid (HA) and tyramine (Tyr). The range may have an upper limit of about 1 mM or less. The solution may comprise from about 0.1 to about 20 w/v % of the conjugate of HA and Tyr. The polymer may comprise a conjugate of a gelatin moiety and a phenol moiety. The gelatin moiety may comprise gelatin and the phenol moiety may comprise 3,4-hydroxyphenylpropionic acid (HPA). The conjugate may have an average degree of phenol substitution of about 13. The phenol moiety may further comprise tyramine. The conjugate may have an average degree of phenol substitution of from about 16 to about 21. The hydrogel may be used for growing cells therein, in which case, the $H_2O_2$ molarity in the solution may be selected to affect differentiation or growth rate of the cells in the hydrogel. The cells may comprise stem cells such as human mesenchymal stem cells. The conjugate may be formed in a process comprising mixing HPA, N-Hydroxysuccinimide (NHS), and 1-ethyl-3(3-dimenthylaminopropyl)-carbodiimide hydrochloride (EDC-HCl) in a mixture to activate phenol groups of HPA; and adding gelatin to the mixture after activation of the phenol groups of HPA, to form a conjugate of gelatin and HPA. The process may further comprise mixing tyramine, NHS, EDC- HCl, and the conjugate of gelatin and HPA in a mixture to form a conjugate of gelatin-HPA-tyramine. The solution may further comprise a drug, a protein, or cells. The solution may be injected to a gelation site.

In accordance with further aspect of the present invention, there is provided a method of forming hydrogels with different crosslinking densities from a polymer comprising a crosslinkable phenol group, comprising mixing the polymer, horseradish peroxidase (HRP), and hydrogen peroxide ($H_2O_2$) in each one of a plurality of solutions, to crosslink the polymer in each solution to form a respective hydrogel, wherein the solutions have a HRP concentration selected to achieve a pre-selected gelation rate and different $H_2O_2$ molarities selected to achieve different crosslinking densities in different hydrogels formed from respective solutions; limiting the $H_2O_2$ molarities to be within a pre-determined range; and limiting the HRP concentration to be above a pre-determined threshold, wherein the pre-determined range and the pre-determined threshold are determined on the basis that, if the $H_2O_2$ molarities in the solutions are limited to be within the range and the HRP concentration in the solutions is limited to be above the threshold, gelation rates in the solutions would be substantially unaffected by variation in the selection of the $H_2O_2$ molarities within the range, and crosslinking densities in the hydrogels would be substantially unaffected by variation in the selection of the HRP concentration above the threshold. The $H_2O_2$ molarity in each solution may be selected so that the respective hydrogel formed from the solution has a pre-selected storage modulus. The polymer may comprise a conjugate of hyaluronic acid (HA) and tyramine (Tyr). The range may have an upper limit of about 1 mM or less. The range may be from about 0.146 to about 1.092 mM. The threshold is about 0.032 unit/ml. Each solution may comprise from about 0.1 to about 20 w/v % of the conjugate of HA and Tyr. The tyramine in each solution may have a molarity of from about 0.42 to about 21 mM. The polymer may comprise a conjugate of a gelatin moiety and a phenol moiety. The gelatin moiety may comprise gelatin and the phenol moiety may comprise 3,4-hydroxyphenylpropionic acid (HPA). The method of claim 33, wherein the conjugate has an average degree of phenol substitution of about 13. The phenol moiety may further comprise tyramine. The hydrogels may be used for growing cells therein, in which case, the $H_2O_2$ molarities in the solutions may be selected to affect differentiation or growth rates of the cells in the hydrogels. The cells may comprise stem cells, such as human mesenchymal stem cells. In this method, HPA, N-Hydroxysuccinimide (NHS), and 1-ethyl-3(3-dimenthylaminopropyl)-carbodiimide hydrochloride (EDC-HCl) may be mixed to activate phenol groups of HPA; and gelatin may be added to the mixture after activation of the phenol groups of HPA, to form a conjugate of gelatin and HPA. The method may further comprise mixing tyramine, NHS, EDC-HCl, and the conjugate of gelatin and HPA to form a conjugate of gelatin-HPA-tyramine.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
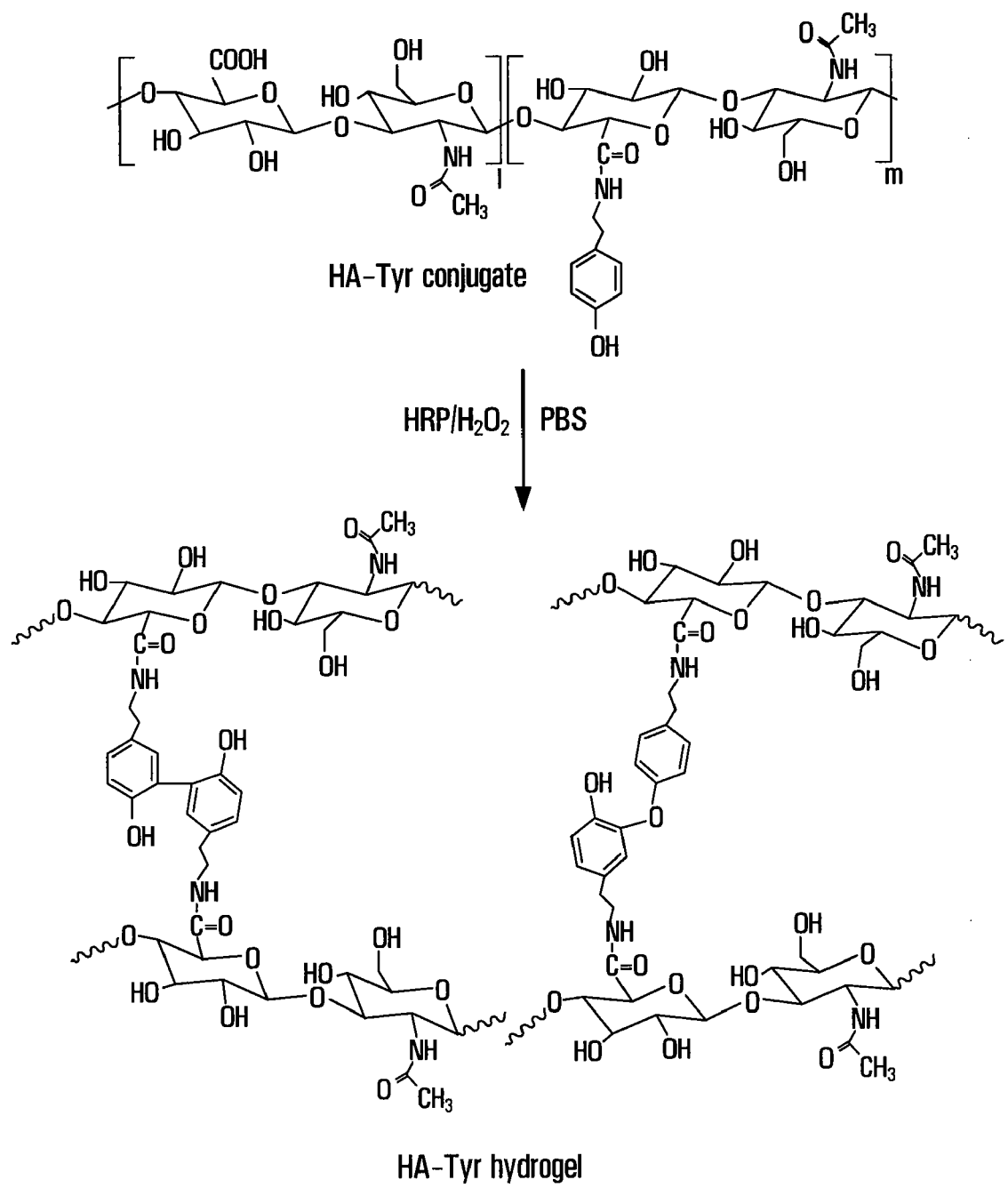
FIG. 1 is a schematic diagram representing a scheme for forming an HA-Tyr hydrogel, exemplary of an embodiment of the present invention.

In brief overview, it has been surprisingly discovered that in the formation of a phenol-containing hydrogel in the presence of horseradish peroxidase (HRP) and a low concentration of hydrogen peroxide ($H_2O_2$), the crosslinking density in the formed hydrogel can be conveniently varied by varying the concentration of $H_2O_2$, without substantially affecting the gelation rate.

As can be understood, a hydrogel includes a polymeric matrix, which can absorb a liquid such as water. As used herein, a hydrogel may refer to either the polymeric matrix with any absorbed liquid, or the polymeric matrix in its dry state (i.e. without absorbed liquid).

In an exemplary embodiment of the present invention, a hydrogel may be formed from a mixture of a polymer, HRP, and $H_2O_2$ in a precursor solution. The polymer has a crosslinkable phenol group. The HRP in the solution is of an effective amount for crosslinking the polymer to form the hydrogel. The $H_2O_2$ in the solution may have a molarity of about 1 mM or less. The $H_2O_2$ molarity may be selected so that the hydrogel formed from the solution has a pre-determined storage modulus. The hydrogel formed from the solution may have a storage modulus from about 10 to about 4000 Pa. The $H_2O_2$ molarity may be from about 0.146 to about 1.092 mM, such as from about 0.16 to about 0.728 mM. The solution may include from about 0.025 to about 1.24 unit/ml of the HRP, such as from about 0.032 to about 0.124 unit/ml, or about 0.062 unit/ml. The polymer may include a conjugate of hyaluronic acid (HA) and tyramine (Tyr), or a conjugate of a gelatin (Gtn) moiety and a phenol moiety. The gelatin moiety may be gelatin, or may include a variant or derivative of gelatin. In some embodiments, the gelatin moiety may contain gelatin and one or more other components, such as a hydrophilic polymeric component (e.g. PEG), a hyaluronic acid, or chitosan. The phenol moiety has a crosslinkable phenol group. The conjugate may be crosslinked through the phenol group. The phenol moiety may include Tyr, or hydroxyphenylpropionic acid (HPA), such as 3,4-hydroxyphenylpropionic acid. The phenol moiety may include both HPA and Tyr. A molar ratio of the $H_2O_2$ to the Tyr in the solution may be about 0.4 or less. The solution may include from about 0.1 to about 20 w/v % of a HA-Tyr conjugate, such as about 1.75 w/v % of the HA-Tyr conjugate. The hyaluronic acid may have a molecular weight of about 90,000 Da. The tyramine in the solution may have a molarity of from about 0.42 to about 21 mM, such as about 2.57 mM. The solution may have a pH of about 4 to about 8. The solution may be at a temperature of about 293 to about 313 K. The solution may further include a drug, protein, or cells. The solution may include water. The solution may include phosphate buffer saline (PBS).

Some exemplary embodiments of the present invention are related to solutions for forming a hyaluronic acid (HA)-tyramine (Tyr) hydrogel. The solution may be referred to as the precursor solution. The precursor solution contains a conjugate of HA and Tyr (HA-Tyr conjugate), HRP, and a low concentration of $H_2O_2$. The $H_2O_2$ may have a molarity of about 1 mM or less in the solution. The ratio of $H_2O_2$ to HRP in the solution may be about 1.8 mol/g or less. The molar ratio of $H_2O_2$ to tyramine moiety in the solution may be about 0.4 or less.

The HA-Tyr conjugate is crosslinkable to form a HA-Tyr hydrogel. The solution may have any suitable concentration of the HA-Tyr conjugate ([HA-Tyr]). In one embodiment, the concentration of HA-Tyr may be selected to obtain desired properties in either the precursor solution or the final hydrogel, or both. For example, the concentration of HA-Tyr may be selected to achieve a desired or suitable viscosity of the precursor solution, such as for injection. The suitable concentration of HA-Tyr may be dependent on the molecular weight of the HA used. For example, in one embodiment, the HA may have a molecular weight of about 90K Da and [HA-Tyr] may be about 1.75 w/v % (weight-volume percent). When the HA has a higher molecular weight, the concentration may need to be lowered to achieve a similar viscosity. In some embodiments, the HA-Tyr concentration may vary in the range of about 0.1 to about 20 w/v %.

The degree of conjugation may also vary, such as from about 1 to about 50. In one embodiment, the degree of conjugation may be 6. The degree of conjugation or substitution (the number of tyramine molecules per 100 repeating units of HA) may be calculated from $^1$H NMR measurement by comparing the ratio of the relative peak integrations of phenyl protons of tyramine (peaks at 7.2 and 6.9 ppm) and the methyl protons of HA (1.9 ppm).

The concentration or molarity of the tyramine moiety ([Tyr]) in the solution may vary depending on the application. In one embodiment, the molarity of tyramine moiety in the solution may vary from about 0.42 to about 21 mM. For example, it may be about 2.57 mM.

The solution contains an effective amount of HRP for crosslinking the conjugate to form the hydrogel. The amount of HRP is typically specified or measured in units (U). One unit of HRP is the amount of HRP that catalyses the reaction of 1 µmol of the substrate in 1 minute under the standard conditions. For example, the solution may contain from about 0.025 to about 1.24 unit/ml, or from about 0.032 to about 0.124 unit/ml, of HRP. The concentration of HRP may also be expressed alternatively in g/ml. For example, HRP may be available in 100 U/mg, in which case the solution may contain from about 0.25 to about 12.4 µg/ml of HRP, such as from about 0.32 to about 1.24 µg/ml.

The concentration of HRP may be selected in order to reach the gel point at a pre-determined time, as will be explained further below. In some embodiments, it may be advantageous to select an optimal HRP concentration to achieve the desired gelation time. For example, to obtain a gelation time of about 40 seconds, the solution may contain about 0.062 unit/ml or 0.62 µg/ml of HRP. When the concentration of HRP in the solution is high, for example at above about 0.032 unit/ml in one embodiment, varying the HRP concentration can change the gelation rate/speed without substantially changing the crosslinking density in the formed hydrogel. When the HRP concentration is low, its variation may affect the gelation rate and the crosslinking density. However, the crosslinking density may be further adjusted by varying the concentration of $H_2O_2$.

In one embodiment, the initial molarity of $H_2O_2$ in the solution prior to gelation ([$H_2O_2$]) may be about 1 mM or less, such as in the range of from about 0.146 to about 1.092 mM, or from about 0.16 to about 0.728 mM. In this case, when the molarity of tyramine is about 2.57 mM, the molar ratio of $H_2O_2$ to tyramine in the solution is about 0.4 or less, such as from about 0.057 to about 0.425, or from about 0.006 to about 0.283.

The solution may further contain other desired additive such as a drug or a protein, depending on the application. The drug may include a therapeutic protein. For example, interferon, herceptin, or the like may be included in the solution. Non-therapeutic proteins, such as α-amylase, lysozyme, or the like, may also be included in the solution. The amount of other additive(s) may be selected depending on the particular application. It should be noted, however, that the addition of other additive(s) may impact on the mechanical strength or other properties of the formed hydrogel or on the formation process, such as the gelation rate. Thus, depending on which and how much other additive(s) are included, the concentration of $H_2O_2$ or HRP, or both, may need to be adjusted to off-set such impact.

The solution may be at a temperature of about 293 to about 313 K, such as at about 310 K (37° C.).

The pH of the solution may be from about 4 to about 8, such as about 7.4.

The solvent in the solution may be any suitable solvent. In one embodiment, the solvent may include water. The solution may also include a phosphate buffer saline (PBS). Other suitable saline solvents may also be used. The solution may also include suitable cell culture medium, suitable buffer, or other solvents of desired properties.

Some exemplary embodiments of the present invention relate to methods of forming a hydrogel. For example, in one embodiment, HA-Tyr conjugate, HRP, and $H_2O_2$ are mixed in a solution to form an HA-Tyr hydrogel. The solution may be a precursor solution described above. In one embodiment, the molarity of $H_2O_2$ in the solution is about 1 mM or less. In another embodiment, the molar ratio of $H_2O_2$ to tyramine in the solution is about 0.4 or less.

The solution may be prepared in any suitable manner. In an exemplary embodiment, an aqueous solution containing a conjugate of HA-Tyr may be first prepared or obtained. The HA-Tyr conjugate and its solution may be prepared in any suitable manner. The concentration of HA-Tyr conjugate in the solution may vary depending on the application. For example, a concentration of HA-Tyr in the range of about 0.1 to about 20 w/v % may be suitable. In some embodiments, HA-Tyr concentration may be in the range of about 1 to about 3 w/v %. Exemplary procedures for forming HA-Tyr conjugate and a suitable solution of HA-Tyr are described in, for example, Kurisawa et al., "Injectable biodegradable hydrogels composed of hyaluronic acid-tyramine conjugates for drug delivery and tissue engineering," *Chemical Communications*, 2005, pp. 4312-4314 (referred to herein as "Kurisawa"); and F. Lee et al., "An injectable enzymatically crosslinked hyaluronic acid-tyramine hydrogel system with independent tuning of mechanical strength and gelation rate," *Soft Matter*, vol. 4, pp. 880-887 (referred to herein as "Lee"), the entire contents of each of which are incorporated herein by reference.

Selected amounts of HRP and $H_2O_2$ may be then added to the solution. The amount of added HRP is selected to crosslink the conjugate to form a hydrogel at a selected gelation rate. Generally, the higher the HRP concentration, the higher the gelation rate. For example, to form the hydrogel in less than about one minute (i.e. reaching the gel point in about 60 seconds), the concentration of HRP in the solution may be about 0.124 unit/ml. The gel point can be defined as the point where the storage modulus (G') and loss modulus (G") of the gel solution are the same (crossover), i.e. G'=G". The gelation rate may be adjusted from about 1 second to about 20 minutes, such as by varying [HRP] from about 0.025 to about 1.24 unit/ml.

The amount of $H_2O_2$ added is selected to adjust or control the crosslinking density in the resulting hydrogel, and thus its mechanical strength which may be measured in terms of its storage modulus (G'). To this end, it has been discovered that when the $H_2O_2$ concentration is low, variation of $[H_2O_2]$ will have no substantial impact on the gelation rate. The gelation rate may be thus adjusted or controlled by varying the HRP concentration. However, when the $H_2O_2$ concentration is too high, its variation can significantly affect both gelation rate and crosslinking density. In some embodiments, reducing $H_2O_2$ below about 1 mM can increase the crosslinking density without materially changing the gelation rate. For example, the molarity of $H_2O_2$ may be selected so that the HA-Tyr hydrogel formed from the solution has a pre-determined storage modulus. The pre-determined storage modulus may vary depending on the particular application. In one embodiment, the pre-determined storage modulus may be in the range of about 10 to about 4000 Pa. The storage modulus of the hydrogel may be measured using any suitable technique. For example, it may be measured using a dynamic mechanical analysis technique, such as an oscillatory rheology technique, as can be understood by persons skilled in the art. Exemplary techniques are described below in the Examples and in Kurisawa and Lee.

In some embodiments, when HRP concentration is varied above a threshold, it may have no substantial impact on the crosslinking density, as discussed above and illustrated in the Examples below.

After the catalysts (HRP and $H_2O_2$) are added, the solution will begin gelation and form a hydrogel within a certain period, such as within about one second to about 20 minutes, depending on the [HRP] in the solution. Gelation should automatically begin after both HRP and $H_2O_2$ are added to the solution and mixed with the HA-Tyr conjugate. However, it should be noted that gelation rate will be dependent on the temperature. At a lower temperature, the gelation process will proceed more slowly.

The solution may be injected into a living body immediately after the catalysts are added, so that the gelation will mainly occur within the body. The body may be a tissue, organism, human body, or another type of living body.

A drug or protein or cells may be added to the solution before gelation and before the solution is injected into the body.

In some embodiments, the precursor solution for the hydrogel may be prepared and the hydrogel may be formed as described in Kurisawa and Lee.

For example, in one embodiment, an aqueous solution of HA-Tyr conjugate with a suitable HA-Tyr concentration may be formed by dissolving a selected amount of HA-Tyr conjugate in a PBS solvent or another suitable solvent as discussed above. The concentration of HA-Tyr may vary in the range of about 0.1 to about 20 w/v %, such as being about 1.75 w/v %. The pH value of the aqueous solution may be adjusted to from about 4 to about 8, such as about 7.4 when a PBS solvent is used. The solution may also be pre-heated to, for example, about 310 K. Selected amounts of HRP and $H_2O_2$ may be added to the solution, depending on the desired gelation speed and crosslinking density. To achieve independent control of gelation speed and crosslinking density, the $H_2O_2$ molarity in the precursor solution may be about 1 mM or less, and the HRP concentration may be 0.032 unit/ml or more. The $H_2O_2$ molarity refers to the molarity as determined by the amount of $H_2O_2$ added to the solution. As would be understood, the molarity of $H_2O_2$ in the solution will change over time due to reaction with HRP. HRP and $H_2O_2$ may be added sequentially or at the same time. Either one of HRP and $H_2O_2$ may be added first. The solution may be mixed by stirring or vortexing during addition of the various ingredients, and optionally thereafter.

Without being limited to any particular theory, it is expected that the hydrogel is formed from the HA-Tyr conjugate in a gelation/crosslinking process in which the tyramine moieties are oxidatively coupled/crosslinked. This crosslinking process is catalyzed by HRP and $H_2O_2$. The crosslinking process is expected to involve two successive steps: first, HRP is oxidized by $H_2O_2$ to form an intermediate; this intermediate then oxidizes the phenol in the conjugate to trigger the crosslinking or coupling of the phenol groups.

Without being limited to any particular theory, it is postulated that when the $H_2O_2$ concentration is too high, it may negatively affect the catalytic activities of the HRP in the solution. When the $H_2O_2$ has a sufficiently low concentration, it likely has negligible effect on HRP activity, and thus will not affect the gelation rate significantly.

Thus, when the amounts of HRP and $H_2O_2$ in the precursor solution are selected with a constraint that the $H_2O_2$ molarity in the precursor solution is within the pre-determined range and the HRP concentration in the precursor solution is above the predetermined threshold, the gelation rate and crosslinking density can be independently adjusted or controlled by selection of the amount of HRP and the amount of $H_2O_2$.

When the concentration of HRP is increased, more HRP enzymes become available to catalyze the crosslinking of tyramines, thus increasing the gelation speed. As the HRP concentration can be used to adjust the gelation rate, fast gelation time can be achieved. As can be appreciated, a faster gelling time may be desirable in some applications. For example, when the solution is administered into a living body to form the hydrogel, such as by subcutaneous injection, faster gelation can provide more localized gel formation than slower gelation. Faster gelation can also reduce uncontrolled diffusion of the gel precursors and the drug molecules to the surrounding tissues, thus reducing the risk of loss of drug material, delivery to unintended site, or overdose.

As can be appreciated, the mechanical strength of the HA-Tyr hydrogel is dependent an its crosslinking density. A stronger hydrogel may be desired as it will degrade slower.

The mechanical strength of HA-Tyr hydrogels has been found to strongly affect their degradation rate in the presence of hyaluronidase in vitro. Hydrogels with higher mechanical strength (crosslinking density) tend to degrade slower. Thus, by adjusting the crosslinking density of the hydrogels, the degradation rate can also be conveniently adjusted without affecting the gelation rate.

It should be understood that embodiments of the present invention is not limited to the formation of HA-Tyr hydrogels. The processes described above can be modified to form other types of hydrogels from a polymer that contains a crosslinkable phenol group. For example, the HA-Tyr conjugate in the above description may be replaced with another polymer that contains a crosslinkable phenol group. The suitable polymers should be water soluable and should have functional groups that can be conjugated with phenol compounds, with a sufficient degree of conjugation, such as about 6 degree of conjugation. For example, the polymer may have functional groups such as hydroxyl, amine, carboxyl groups, or the like. Suitable polymers may include dextran, chitin, chitoson, heparin, gelatin, collagen, or the like.

It is expected that independent control of crosslinking density and gelation rate by adjusting the respective concentrations of $H_2O_2$ and HRP can be achieved for a variety of polymers that can be crosslinked to form hydrogels in the presence of $H_2O_2$ and HRP as the catalyst. Generally, for a given polymer and given desired hydrogel properties, the range for $H_2O_2$ molarity in the precursor solution and the threshold for HRP concentration in the precursor solution for achieving independent control may be pre-determined or obtained. Independent control can then be achieved by limiting the $H_2O_2$ molarity in the precursor solution to be within the pre-determined range for $H_2O_2$ molarity and limiting the HRP concentration in the precursor solution to be above the pre-determined threshold for the HRP concentration.

For example, hydrogels with different crosslinking densities may be formed from a polymer that includes a crosslinkable phenol group as follows. A number of different precursor solutions are provided. In each solution, the polymer, HRP, and $H_2O_2$ are mixed to crosslink the polymer to form a respective hydrogel. The different solutions have about the same HRP concentration, which is selected to achieve a pre-selected gelation rate, and different $H_2O_2$ molarities, which are selected to achieve different crosslinking densities in different hydrogels formed from the respective precursor solutions. The $H_2O_2$ molarities are limited to within the pre-determined $H_2O_2$ molarity range, and the HRP concentration is limited to above the pre-determined HRP concentration threshold. The pre-determined range and threshold are determined on the basis that, if the $H_2O_2$ molarities in the solutions are limited to be within the range and the HRP concentration in the solutions is limited to be above the threshold, gelation rates in the solutions would be substantially unaffected by variation in the selection of the $H_2O_2$ molarities within the range, and crosslinking densities in the resulting hydrogels would be substantially unaffected by variation in the selection of the HRP concentration above the threshold. The $H_2O_2$ molarity in each respective solution may be selected so that the respective hydrogel formed from the respective solution has a pre-determined storage modulus. The polymer may include a HA-Tyr conjugate, or a conjugate of a gelatin moiety and a phenol moiety.

In an exemplary process, the range of $H_2O_2$ molarity and the threshold of HRP concentration for achieving independent control of mechanical property and gelation rate may be determined as follows. Different hydrogels are formed from different precursor solutions that include a particular polymer. Each precursor solution includes respective selected amounts of the particular polymer to be used, HRP, and $H_2O_2$. The solutions have the same concentration of the polymer. Some of the solutions have the same $H_2O_2$ molarity but different HRP concentrations. Some of the solutions have the same HRP concentration but different $H_2O_2$ molarities. The different $H_2O_2$ molarities and HRP concentrations should vary sufficiently widely to ensure that reliable results will be achieved. Different hydrogels are formed from the respective solutions. A first metric indicative of the gelation rate, such as the time required to reach gel point, is measured in each solution during formation of the hydrogel. A second metric indicative of the crosslinking density in each formed hydrogel, such as storage modulus, is also measured. Other suitable metrics may also be used. The range for $H_2O_2$ molarity and the threshold for HRP concentration can then be determined by requiring that (1) the first metric is substantially constant for solutions that have the same HRP concentration above the threshold but have different $H_2O_2$ molarities each within the range, and (2) the second metric is substantially constant for solutions that have the same $H_2O_2$ molarity within the range but have different HRP concentrations each above the threshold.

As used herein, values of a physical or chemical quantity or measurement are considered the same, equal, or constant, when the values are substantially the same. That is, any difference between the values has no material effect on the outcome of the relevant procedure, or the difference is within the typical error range of the measurement technique used.

The determined range and threshold may then be used in other applications. The proper range and threshold for a particular polymer and reaction conditions may also be determined by extrapolation from known data for other polymers or known data for the same polymer but different reaction conditions. The appropriateness of a given range and threshold for a particular polymer and reaction conditions may be verified by routine testing, as can be understood by those skilled in the art in view of this document.

Once the range and threshold has been determined, appropriate amounts of HRP and $H_2O_2$ may be selected. A suitable amount of the polymer, the selected amounts of HRP and $H_2O_2$ may be mixed in a precursor solution to crosslink the polymer to form the hydrogel. The amounts of HRP and $H_2O_2$ are selected to limit the $H_2O_2$ molarity in the solution to be within the pre-determined range and to limit the HRP concentration in the solution to be above the pre-determined threshold.

In an exemplary embodiment of the present invention, the polymer matrix of the hydrogel may be formed of a crosslinked conjugate of a gelatin (Gtn) moiety and a phenol moiety.

The gelatin moiety in the conjugate may be gelatin, and may include a variant or derivative of gelatin. In some embodiments, the gelatin moiety may contain gelatin and one or more other components, such as a hydroplilic polymeric component (e.g. PEG), a hyaluronic acid, or chitosan.

The phenol moiety in the conjugate has a crosslinkable phenol group. The conjugates are crosslinked through the phenol groups. In one specific embodiment, the phenol moiety is hydroxyphenylpropionic acid (HPA), such as 3,4-hydroxyphenylpropionic acid. In another specific embodiment, the phenol moiety includes tyramine (Tyr). In further specific embodiment, the phenol moiety includes both HPA and Tyr. Thus, in different embodiments, the hydrogel may be a Gtn-HPA hydrogel, a Gtn-Tyr hydrogel, or a Gtn-HPA-Tyr hydrogel. The weight ratio of HPA to Tyr in a Gtn-HPA-Tyr hydrogel may be from about 0.01 to 100. In some embodiments, the phenol moiety may be other types of moieties that contain sufficient crosslinkable phenol groups.

A Gtn-HPA hydrogel may be conveniently formed utilizing the oxidative coupling of HPA moieties catalyzed by $H_2O_2$ and HRP. Phenols can crosslink through either a C—C linkage between the ortho-carbons of the aromatic ring or a C—O linkage between the ortho-carbon and the phenolic oxygen. The hydrogel may contain one or more other components, either incorporated into the matrix or in a liquid in the hydrogel.

As will become clear below, with sufficient crosslinkable phenol groups in the phenol moiety, the conjugates may be conveniently crosslinked through the phenol groups to form the hydrogel in an enzyme-mediated oxidation crosslinking process, in the presence of horseradish peroxidase (HRP) and hydrogen peroxide ($H_2O_2$). It is not necessary to utilize physical crosslinking or chemical crosslinkers that would introduce cytotoxicity and reduce bioactivity of the surrounding biological agents. The hydrogel can be made stable in various biological environments, and can have high biocompatibility and low biodegradability. The mechanical properties of the hydrogel can be conveniently adjusted or controlled during the formation process.

In further embodiments, an exemplary hydrogel may be conveniently formed by crosslinking the conjugates in the presence of HRP and $H_2O_2$.

The conjugates may be obtained or formed prior to crosslinking. For example, Gtn-HPA conjugates may be formed according to the synthesis route described in the Examples below, and may utilize a general carbodiimide/active ester-mediated coupling reaction. The coupling reaction may be conducted in water, which may be distilled water.

In an exemplary procedure, suitable amounts of HPA, N-Hydroxysuccinimide (NHS), and 1-ethyl-3(3-dimenthylaminopropyl)-carbodiimide hydrochloride (EDC-HCl) are dissolved in a mixture of distilled water and DMF to form a first solution. The suitable amount for each component may be selected by those skilled in the art in a particular application.

The first solution is stirred at room temperature for a sufficient time, such as about 5 hours, to allow the phenol groups in the phenol moiety to become activated. The pH of the solution may be maintained at about 4.7 during this period, as in a standard carbodiimide mediated reaction.

A second solution containing dissolved Gtn moiety is then mixed with the first solution. The second solution may be an aqueous solution, and may have a Gtn concentration of about 1 to about 95 wt %.

The mixture solution may have various suitable concentrations of Gtn, HPA, NHS, and EDC-HCl, respectively. The ratio of Gtn to HPA may be selected to obtain the desired degree of substitution of amino groups of Gtn by the phenol moiety.

The degree of substitution, or more specifically the degree of phenol substitution, refers to the number of phenol molecules per 100 amino acid residues of Gtn in the conjugate. The average degree of substitution may be determined by a conventional 2,4,6-trinitrobenzene sulfonic acid (TNBS) technique. See for example, a description of the technique in S. L. Snyder et al., "An improved 2,4,6-trinitrobenzene sulfonic acid method for the determination of amines," *Analytical Biochemistry*, 1975, vol. 64, pp. 284-288.

The mixture solution is stirred for a sufficient time, such as about 8 to about 10 hours, to allow the conjugate to form.

The mixture solution is then purified. For example, it may be dialyzed in dialysis tubes against sodium chloride for about two days, a mixture of distilled water and ethanol for one day, and then distilled water for one day, in the about order. This purification procedure can effectively remove unconjugated phenol compounds from the mixture solution.

The purified solution may be lyophilized to obtain the Gtn-HPA conjugate in solid form.

The above exemplary procedure for preparing the conjugate can conveniently prevent activation of the amine groups of Gtn. Activated amine groups in Gtn could cause undesired inter or intra-molecular coupling between Gtn molecules. In the above procedure, the carboxyl groups of HPA are activated first. The Gtn is added to the reaction mixture only after completion of the active ester reaction. As a result, the amine groups of Gtn will react with activated HPA-NHS; and become substituted by HPA. In this procedure, it is possible to obtain a high degree of HPA substitution, such as up to about, and about 90% of the amine groups in Gtn can be conjugated with HPA.

Optionally, to further increase the phenol moiety content in the conjugate, Tyr may be incorporated into the Gtn-HPA conjugate, through reactions between the amine group of Tyr and the carboxyl group of Gtn. The Tyr may be added to the mixture solution after the conjugate Gtn-HPA has formed, either before or after the purification procedure. The exemplary reaction route is further described in the Examples. Tyr, and additional NHS and EDC.HCl may be added to the solution containing the Gtn-HPA conjugate.

The total ratio of the number of phenol groups (in both HPA and Tyr) to the number of the aromatic rings of Gtn can be significantly increased by the addition of Tyr to the conjugate. For example, the total average degree of substitution in Gtn-HPA-Tyr conjugates may be from about 16 to about 21, as compared to 13 in Gtn-HPA conjugates. The average degree of substitution in Gtn-HPA-Tyr conjugates may be calculated from $^1H$ NMR measurements, as can be understood by those skilled in the art.

The above procedures may be modified or adapted to prepare other suitable types of Gtn-phenol conjugates.

To crosslink the Gtn-phenol conjugates to form the hydrogel, the conjugates, HRP and $H_2O_2$ may be mixed in a liquid mixture solution.

In an exemplary embodiment, the crosslinking process is catalyzed and mediated by enzyme HRP and $H_2O_2$. Without being limited to any specific theory, it is expected that the crosslinking process in the mixture involves two successive steps: HRP is initially oxidized by $H_2O_2$ to form an intermediate; the intermediate then oxidizes the phenol groups of the conjugates to effect the crosslinking between the conjugates through the phenol groups.

The gelation rate (or speed of crosslinking) is dependent on the concentration of HRP ([HRP]) in the mixture, and can be affected or controlled by adjusting [HRP]. The crosslinking density in the resulting hydrogel is dependent on the concentration of $H_2O_2$ ($[H_2O_2]$) in the mixture, likely because the enzyme activity of HRP is affected by $[H_2O_2]$. Thus, conveniently, the mechanical properties, such as mechanical strength, of the hydrogel can be affected or controlled by adjusting $[H_2O_2]$. Further, when [HRP] is sufficiently high (and the gelation process is fast), variation in $[H_2O_2]$ will not substantially affect the gelation rate. Thus, a pre-determined mechanical property value, such as a pre-selected storage modulus, of the hydrogel may be achieved by selecting an appropriated value for $[H_2O_2]$.

The raw materials, reagents and catalysts for forming the conjugate and the Gtn-phenol hydrogel can be readily obtained from commercial sources, and can be separately prepared using conventional synthesis procedures by those skilled in the art. However, the above described procedures for preparing the Gtn-phenol conjugates may provide some additional benefits, such as increased degree of phenol substitution.

It has also been found that the degradability of Gtn-hydrogels by collagenase is correlated with hydrogel stiffness. When the hydrogel is less stiff, it degrades faster. Thus, depending on the particular application, the $H_2O_2$ concentration in the hydrogel formation mixture may be selected to control the degradability (degradation rate and mode) of the resulting hydrogel. In turn, as the degradability of the Gtn-phenol hydrogel can affect both tissue regeneration and drug release profile, properly adjusting the $H_2O_2$ concentration can produce desired effects on tissue regeneration or drug release profile in the resulting hydrogel.

It has been found that the crosslinking process with HRP enzyme-mediated oxidation does not give rise to cytotoxicity. Thus, this process can be safely performed in a biological environment.

Accordingly, in different embodiments, the hydrogel may form either outside or inside a biological subject. For example, the precursor liquid mixture may be prepared and aged outside the subject to form the hydrogel. The hydrogel may then be injected into a biological subject, such as a tissue, organ, or live body.

In another example, the liquid formation mixture may be injected immediately after the various ingredients are mixed, and before gelation has been substantially completed.

In a further example, different ingredient solutions may be separately injected into the same region of the subject to allow the solutions to mix and form the precursor mixture inside the subject.

The liquid mixture for forming the hydrogel or its components can be conveniently introduced to a gelation site by injection. The gelation site may be inside a biological subject, such as tissue or organism. The liquid mixture may be pre-mixed and then injected. Alternatively, components of the liquid mixture may be separately injected, either sequentially or simultaneously, so that they will separately reach, and then mix at, the gelation site. In the latter approach, the onset time of crosslinking/gelation can be conveniently controlled. It can also avoid premature crosslinking/gelation before the reactants reach the desired gelation site.

The hydrogels formed according an embodiment described herein may be used for growing cells. For this purpose, the cells may be dispersed in the precursor solution before crosslinking is completed. Alternatively, cells may be introduced into the formed hydrogel at a later stage.

Some cells, such as stem cells, can differentiate into different cell types. The differentiation of cells in a hydrogel may depend on the mechanical properties, such as stiffness, of the hydrogel. For example, the stiffness of the hydrogel may be used to affect or control differentiation of stem cells such as human mesenchymal stem cells (hMSCs), embryonic stems cells, neuronal stem cells, induced pluripotent stem (IPS) cells, or the like. Engler A. J. et al. discuss how stiffness of a hydrogel substrate can affect cell differentiation of hMSCs, in "Matrix elasticity directs stem cell lineage specification," *Cell*, 2006, vol. 126, pp. 677-687, the entire content of which is incorporated herein by reference.

As discussed above, the mechanical properties of the hydrogel are dependent on the crosslinking density and thus can be affected or controlled by adjusting the $H_2O_2$ molarity in the precursor solution. Therefore, when the cells are capable of differentiating into a plurality of cell types, the $H_2O_2$ molarity in the precursor solution may be conveniently selected to promote the differentiation of the cells into a selected cell type. For different hydrogels, different $H_2O_2$ molarities may be selected to affect or control the differentiation of the cells in the hydrogels. That is, the $H_2O_2$ molarity in each respective precursor solution may be selected so that the cells in the corresponding hydrogel will tend to differentiate into a respective selected cell type.

Further, the cells may grow at different rates in hydrogels with different mechanical strengths. Thus, the $H_2O_2$ molarities in the precursor solutions can also be selected to affect or control the growth rates of the cells in the respective hydrogels. That is, the $H_2O_2$ molarities may be selected so that the cells in a respective hydrogel will grow at a growth rate within a respective pre-selected growth rate range. As discussed herein, the higher the $H_2O_2$ molarities, the higher the crosslinking densities, and hence the stiffer the hydrogel. For many types of cells, the cell growth rate is lower in a softer hydrogel. Therefore, for such cells, increasing the $H_2O_2$ molarity in the precursor solution will produce a hydrogel in which the cells will grow at a reduced rate.

As the mechanical strength of the hydrogel can be conveniently adjusted independent of the gelation rate, the differentiation and proliferation of the cells in the hydrogels may be conveniently adjusted or controlled, as described herein.

Thus, an exemplary embodiment of the present invention relates to a method of growing or differentiating cells in a hydrogel, in which the hydrogel is formed from a precursor solution for forming the hydrogel as described herein. The cells are dispersed in the precursor solution. The HRP concentration in the precursor solution is selected to control the gelation rate. The $H_2O_2$ molarity in the precursor solution is selected to control the crosslinking density, and thus differentiation or growth rate of the cells, in the hydrogel. The HRP concentration is limited to be above a pre-determined threshold and the $H_2O_2$ molarity is limited to be within a pre-determined range, so that the gelation rate is adjustable, by varying the HRP concentration, without substantially affecting the crosslinking density and hence the differentiation or growth rate of the cells in the hydrogel; and the crosslinking density and hence the differentiation or growth rate of the cells in the hydrogel is adjustable, by varying the $H_2O_2$ molarity, without substantially affecting the gelation rate. The range and threshold may be pre-determined as described herein. Conveniently, in this embodiment, the gelation rate and cell growth/differentiation can be independently controlled by selecting the appropriate $H_2O_2$ molarity and HRP concentration.

Exemplary Gtn-phenol hydrogels described herein can be used to provide a support or scaffold for cell growth, either within or outside a biological subject. The hydrogel can also be utilized as a soft tissue engineering scaffold.

Hydrogels with different mechanical properties may be conveniently formed and used for cell cultivation/differentiation in two-dimension (2D) or three-dimension (3D), and for effective regeneration of tissue.

As can be appreciated, the hydrogels may be formed in-situ, and the precursors for the hydrogels and other ingredients may be injected or administered to the gelation site (the site at which the hydrogel forms), such as by using a needle or a syringe.

It is possible to inject a hydrogel (such as Gtn-HPA) precursor solution containing bioactive agents such as cells and proteins. It has been experimentally confirmed that the enzyme-mediated oxidation and crosslinking process does not involve significant cytotoxicity and does not cause substantial loss of protein activity. Moreover, the rate of hydrogel formation can be conveniently affected or controlled by adjusting HRP concentration and can be fast enough to prevent uncontrolled diffusion of bioactive agents to surrounding tissues before the hydrogel is formed.

In another embodiment, cells, such as hMSCs are cultured or differentiated in the Gtn-phenol hydrogels. The cells may be cultured on a surface of the hydrogel, or inside the hydrogel. The surface may be an exterior surface or an interior surface, such as a pore surface of the hydrogel.

The exemplary hydrogels are suitable for many biological applications due to gelatin's biodegradability and biocompatibility. They are also suitable for many tissue engineering applications, as Gtn has positively charged residues and RGD (Arginine-Glycine-Aspartic Acid) groups, which can facilitate the attachment of cells to the matrix. For example, the exemplary hydrogels may be combined with cells to form artificial tissues.

Conveniently, the exemplary hydrogels are suitable for cell cultivation and differentiation, as they have low or no cytotoxicity and are relatively stable. In addition, the rate of cell growth and differentiation of stem cells may be conveniently affected or controlled by changing $H_2O_2$ molarity/concentration in the precursor solution. As discussed above, the mechanical properties of the hydrogel can be affected or controlled by changing $H_2O_2$ molarity/concentration without substantially affecting the gelation rate. Further, tests show that hMSCs growth/differentiation on the surface of Gtn-HPA hydrogel is strongly dependent on the hydrogel stiffness. It has been found that hMSCs attached to surfaces of Gtn-HPA hydrogels with different hydrogel stiffness differentiate to different specific phenotypes, such as neuronal and muscle cells. Three-dimensional (3D) hMSCs cultures can be cultured and differentiated in Gtn-HPA hydrogels with stiffness as low as 281 Pa of G'. Tests show that hMSCs can grow well and differentiate to only neuronal cells in soft Gtn-HPA hydrogels.

Exemplary embodiments of the present invention may be used to implant hydrogels encapsulated with cell or protein and to regenerate tissue/organ effectively. The regeneration of tissue can be effective due to the biocompatibility and biodegradability of the hydrogel. For example, the hydrogels can be implanted into damaged or injured site in a living body. The hydrogel precursor solution with cells and proteins may be injected into the desired site in the body, providing cell cultivation and differentiation in a 3D environment.

The exemplary hydrogels described herein, including injected hydrogels, may also be used for drug delivery. A drug may be incorporated or imbedded in the hydrogel such that it is releasable under appropriate conditions. For example, a drug may be dispersed in the hydrogel. The drug may include a bioactive or therapeutic protein. The hydrogel with the drug may be then placed adjacent a delivery site to allow the drug to release from the hydrogel into the delivery site. A hydrogel formed according to an embodiment of the present invention may be used to provide a sustained-release system to prolong the effects of the bioactive or therapeutic protein in vivo.

The rate of diffusion release of a drug, protein or other molecules encapsulated in the hydrogel may be dependent on the crosslinking density in the hydrogel. Thus, by adjusting the crosslinking density, a desired delivery or release rate may be obtained. As the crosslinking density may be tuned by adjusting $[H_2O_2]$ without materially affecting the gelation rate during hydrogel formation, desired mechanical strength or delivery rate may be achieved without compromising, such as slowing down, the gelation rate. It has been demonstrated by tests that the molarity of $H_2O_2$ could be used to adjust or control the release rate of proteins, such as α-amylase and lysozyme. It has been found that the release of α-amylase from sample hydrogels was diffusion-controlled and its release rate decreased with increasing crosslinking density. Lysozymes can interact with hyaluronic acid electrostatically; hence, degradation of the hydrogel network by hyaluronidase may be utilized to achieve sustained release.

Embodiments of the present invention may be advantageously utilized in a wide range of applications, in addition to cell growth, tissue regeneration, or drug delivery.

The following non-limiting examples further illustrate exemplary embodiments described herein.

EXAMPLES

The materials used in the Examples were obtained as follows unless otherwise specified in the specific example.

Sodium hyaluronate 90 kDa was provided by Chisso Corporation™ of Tokyo, Japan.

Tyramine hydrochloride (Tyr-HCl), N-Hydroxysuccinimide (NHS), 1-Ethyl-3-(3-dimethylaminopropyl)-carbodiimide hydrochloride (EDC.HCl), sodium chloride, 5-aminofluorescein, dimethyl sulfoxide (DMSO), lysozyme from chicken egg white, α-amylase from *Bacillus amyloliquefaciens*, hyaluronidase from bovine testes, bovine serum albumin (BSA), polyoxyethylene-sorbitan monolaurate (Tween 20), *Micrococcus lysodeikticus*, 3,4-hydroxyphenylpropionic acid, Triton X-100, anti-β-tubulin, anti-neurofilament light chain (NFL), anti-microtubule associated protein 2 (MAP2), and type I collagenase (246 units/mg) were obtained from Sigma-Aldrich™.

Sodium tetraborate.10H2O and carbazole and D-glucuronic acid were obtained from Fluka™.

Alexa Fluor 680 conjugated BSA (SAIVI Alexa Fluor™ 680) and Alexa Fluor 680 carboxylic acid succinimidyl ester were purchased from Invitrogen™.

Hydrogen peroxide ($H_2O_2$) was obtained from Lancaster™.

Gelatin (Gtn) (MW=80-140 kDa, pI=5) and Horseradish peroxidase (HRP, 100 unit/mg) were obtained from Wako Pure Chemical Industries™

Polyclonal antibody to *Bacillus amyloliquefaciens* α-amylase (biotin) was purchased from Acris Antibodies™.

Polyclonal antibody to chicken lysozyme (biotin) was purchased from United States Biological™.

Streptavidin alkaline phosphate conjugated and p-Nitrophenyl phosphate (p-NPP) were purchased from Chemicon™.

PBS (150 mM, pH 7.3) was supplied by the media preparation facility in Biopolis, Singapore.

Anti-neruofilament heavy chain was obtained from Zymed™.

Human mesenchymal stem cells (hMSCs) were provided by Cambrex Bio Science Walkersville, Inc. (USA).

Human fibroblast (HFF-1) cells were obtained from ATCC (USA).

Mesencult human basal medium supplemented with mesencult human supplement was purchased by Stem Cell Technologies™ (Canada).

Dulbecco's modified eagle medium (DMEM), fetal bovine serum (FBS), calcein acetoxymethyl ester, 4',6-diamidino-2-phenylindole (DAPI) and fluorophore-conjugated secondary antibodies were provided by Invitrogen™ (Singapore).

HRP-conjugated secondary antibodies were purchased from GE Healthcare (Singapore).

Example I

Example I-A

Synthesis of HA-Tyr Conjugate

Solutions of HA-Tyr conjugate were prepared according to the procedures described in Kurisawa and Lee, with some modifications as described below. The modification was related to the condensation agents and the purification step to more effectively remove un-reacted tyramine.

HA (1 g, 2.5 mmol) was dissolved in 100 ml of distilled water, forming an initial solution. Tyramine hydrochloride (202 mg, 1.2 mmol) was first added to this solution. EDC.HCl (479 mg, 2.5 mmol) and NHS (290 mg, 2.5 mmol) were then added to initiate the conjugation reaction. As the reaction proceeded, the pH of the mixture was maintained at 4.7 with 0.1 M NaOH. The reaction mixture was stirred overnight at room temperature and then the pH was brought to 7.0. The solution was transferred to dialysis tubes with molecular cut-off of 1000 Da. The tubes were dialyzed against 100 mM sodium chloride solution for 2 days; a mixture of distilled water and ethanol (3:1) was used for the first day and distilled water was used for the next day. The purified solution was lyophilized to obtain HA-Tyr conjugates. The degree of substitution was calculated from $^1H$ NMR measurement by comparing the ratio of the relative peak integrations of phenyl protons of tyramine and the methyl protons of HA. The degree of substitution was found to be 6.

Example I-B

Synthesis of Fluorescent-Labeled HA-Tyr Conjugate

HA (1 g, 2.5 mmol) was dissolved in 100 ml of distilled water, forming an initial solution. Tyramine hydrochloride (162 mg, 0.93 mmol) and 5-aminofluorescein (81 mg, 0.23 mmol in 1.62 ml DMSO) were added to this solution. EDC.HCl (479 mg, 2.5 mmol) and NHS (290 mg, 2.5 mmol) were then added and the pH of the mixture was maintained at 4.7 with 0.1 M NaOH. The solution was stirred overnight at room temperature and then brought to pH 7.0. The solution was next filtered with grade 1 Whatman™ cellulose filter paper to remove unconjugated aminofluorescein that had precipitated. The filtrate was collected into dialysis tubes of molecular cut-off 3500 Da. Then the dialysis and lyophilization procedures described in Example I-A were carried out. The degree of substitution of tyramine was calculated from 1H NMR and the degree of aminofluorescein conjugated was estimated by comparing the absorbance value at 490 nm of 1 mg/ml fluorescence-conjugated HA-Tyr solution to a set of aminofluorescein standards. The degrees of substitution of tyramine and aminofluorescein were 4 and 0.4, respectively.

Example I-C

Synthesis of HA-Tyr Hydrogels

An aqueous solution of HA-Tyr was formed by dissolving 1 ml of a solution of HA-Tyr, as prepared in Examples I-A and I-B, in PBS, where the final concentration of HA-Tyr was 1.75 w/v %. The aqueous solution had a pH of about 7.4 and was pre-heated to about 310 K. Different amounts of HRP and $H_2O_2$ were added sequentially to the solution. The solution was then vortexed and immediately applied to a bottom plate for a Rheoscope, whereon the HA-Tyr conjugate in the solution was crosslinked to form an HA-Tyr hydrogel.

The formation of the HA-Tyr hydrogel was schematically represented in FIG. 1. As can be understood, this scheme involves an enzyme-mediated oxidation reaction in which the phenol groups/derivatives of the tyramine were crosslinked.

Rheological measurements of the hydrogel formation were performed with a HAAKE™ Rheoscope 1 rheometer (Karlsruhe, Germany) using a cone and plate geometry of 6 cm diameter and 0.903° cone angle. The measurements were taken at 310 K in the dynamic oscillatory mode with a constant deformation of 1% and frequency of 1 Hz. To avoid slippage of samples during the measurement, the bottom plate was made of roughened glass.

After the solution was applied to the bottom plate, the upper cone was then lowered to a measurement gap of 0.024 mm and a layer of silicon oil was carefully applied around the cone to prevent solvent evaporation during the experiment. The measurement parameters were determined to be within the linear viscoelastic region in preliminary experiments. Measurement was allowed to proceed until G' reached a plateau. Next, a frequency sweep was performed with a constant shear stress predetermined to induce a 10% deformation at 1 Hz. Also, a strain sweep of increasing deformation from 1 to 100% was performed at 1 Hz.

Figure 2:
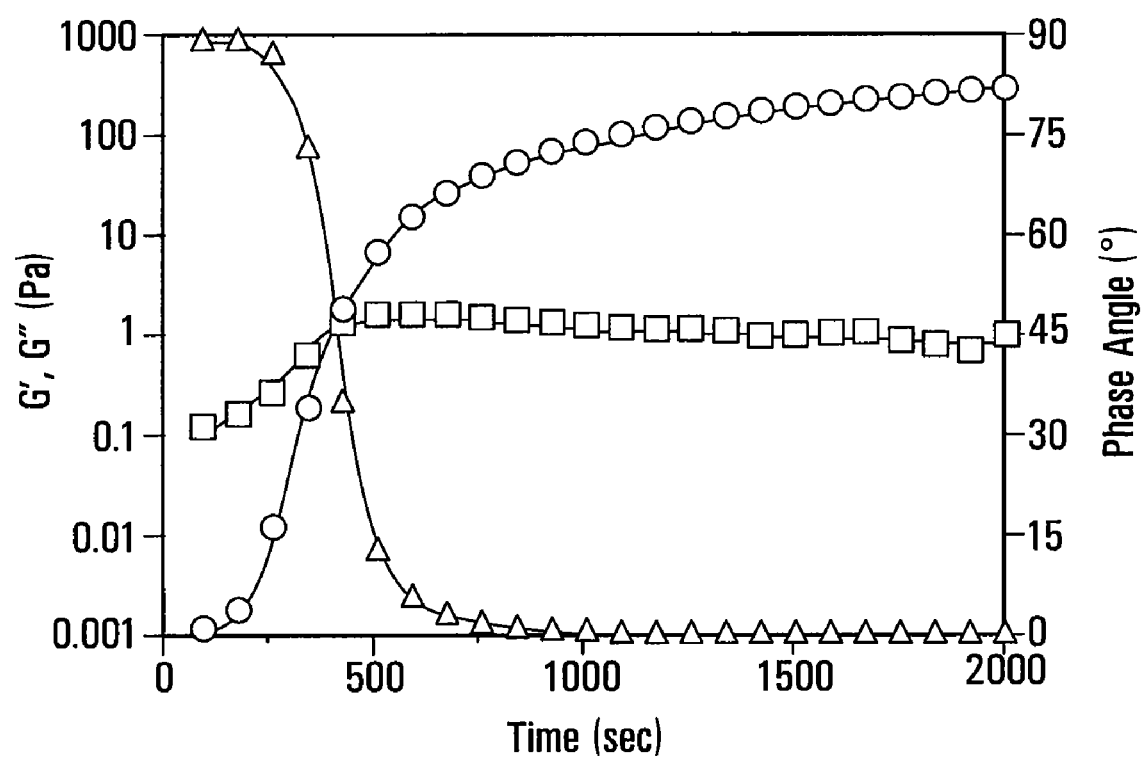
FIGS. 2, 3, 4 and 5 are line graphs showing representative measurement results obtained from samples prepared according an exemplary embodiment of the present invention.

Representative measurement results obtained with the oscillatory rheometry, from a solution containing about 1.75 w/v % of HA-Tyr conjugate, about 0.728 mM of $H_2O_2$, and about 0.025 unit/ml of HRP, are shown in FIG. 2. The results shown in FIG. 2 include measured storage modulus G' (circles), loss modulus G" (squares) and phase angle δ (triangles) as a function of time. As can be seen, at the beginning of the crosslinking process, G" was two orders of magnitude greater than G' and the phase angle was at 90°, indicating a predominantly viscous material. As time progressed, both G' and G" increased and crossover of the two moduli occurred at about 45° phase angle.

This crossover point can be regarded as the gel point. The gel point is also the transition point from a viscoelastic liquid to a viscoelastic solid. The time period between the beginning of crosslinking and the gel point is used herein as an indicator of the gelation rate or gelation speed.

After the gel point, G' continued to increase and eventually reached a plateau at which the phase angle was close to zero, indicating a solid-like elastic material.

Table I lists the gel points and corresponding HRP concentrations for samples tested with the $H_2O_2$ concentration fixed at about 0.728 mM.

TABLE I

Gel Point and HRP concentration ($[H_2O_2]$ = 0.728 mM)

| HRP (unit/ml) | Gel Point, G' = G" (s) |
|---|---|
| 0.008 | 1183 |
| 0.016 | 567 |
| 0.031 | 267 |
| 0.062 | 122 |
| 0.124 | 48 |

Table II lists the final storage modulus and corresponding $H_2O_2$ concentrations for samples tested with the HRP concentration fixed at about 0.62 unit/ml.

TABLE II

Storage Modulus at different $H_2O_2$ concentrations with [HRP] = 0.062 unit/ml

| $H_2O_2$ (mM) | G' |
|---|---|
| 0.146 | 7.7 |
| 0.291 | 265 |
| 0.437 | 857 |
| 0.582 | 1512 |
| 0.728 | 2700 |
| 1.092 | 3798 |
| 1.456 | 2518 |
| 2.912 | 578 |

Figure 3:
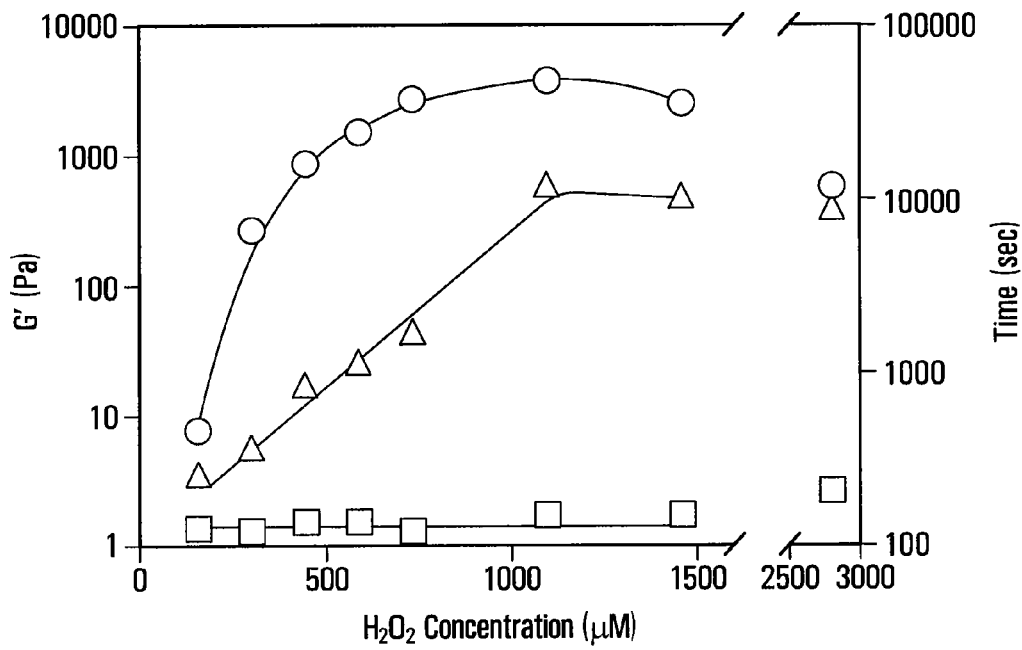

FIG. 3 shows the dependency of the gelation rate as indicated by the gel point (squares), the time required for G' to reach the plateau (triangles), and the final G' value (circles), on the $H_2O_2$ concentration, respectively. These results were obtained from precursor solutions with a constant HRP concentration at about 0.062 unit/ml, and various $H_2O_2$ concentrations as shown, which increased from about 0.146 mM to about 1.092 mM.

As can be seen, the gel point remained substantially constant at about 130 seconds, indicating that the gelation rate was independent of $H_2O_2$ concentration.

The time required for G' to reach the plateau, i.e. the time needed to form all the possible tyramine crosslinks, increased with $H_2O_2$ concentration, suggesting that HRP was continuously oxidized by $H_2O_2$ and reduced by tyramine until all $H_2O_2$ has been depleted. G' peaked at about 1.092 mM of $H_2O_2$ and further increase in $H_2O_2$ concentration resulted in decreased G'. Such decrease may be due to de-activation of HRP by the excessive $H_2O_2$. At the given concentration of HRP, different $H_2O_2$ concentrations at about 1 mM or less produced HA-Tyr hydrogels with different crosslinking densities and hence mechanical strengths, without substantially affecting the gelation rate.

Figure 4:
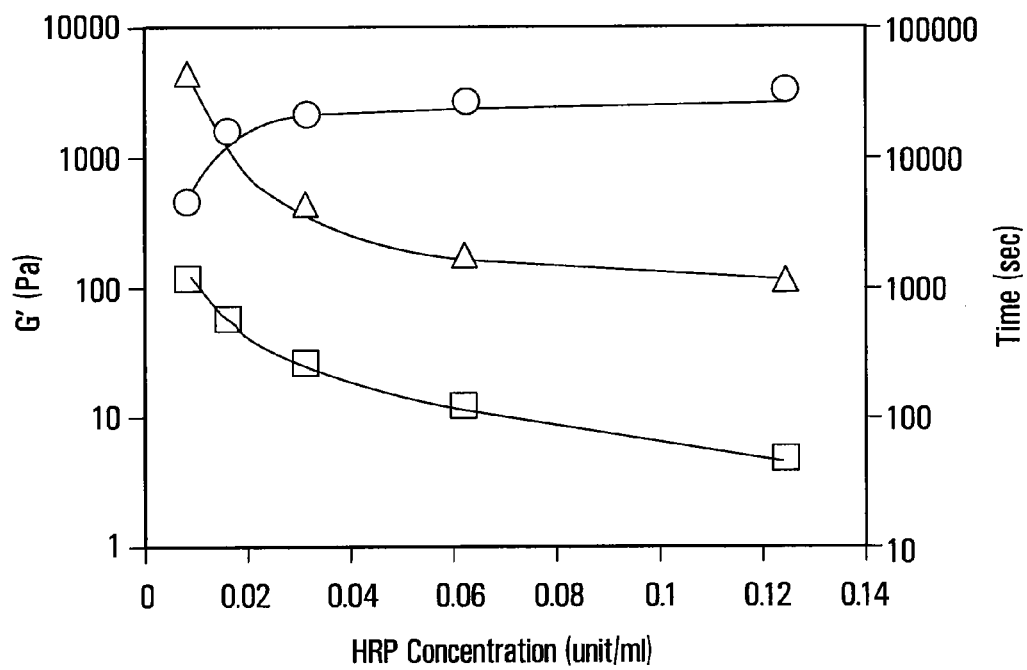

FIG. 4 shows the dependency of the gel point (squares) and the time required for G' to reach the plateau (triangles), and the final G' value (circles) on HRP concentration, at a fixed $H_2O_2$ concentration of 0.728 mM. Both the gel point and the time required for G' to reach the plateau decreased with an increasing HRP concentration. At 0.124 unit/ml of HRP, the gel point was reached within about 60 seconds. Tests showed that at a concentration of HRP of about 1.24 unit/ml, hydrogel was formed within about one second (data not shown in FIG. 4).

The values of G' remained relatively constant above 0.032 unit/ml of HRP concentration, indicating that the change of HRP concentration above about 0.032 unit/ml did not substantially affect the crosslinking density or mechanical strength of the formed hydrogels.

The effects of frequency and strain on G' of the sample hydrogels were also investigated. Frequency sweeps were performed on sample HA-Tyr hydrogels formed with various concentrations of $H_2O_2$ at fixed HRP concentration (about 0.062 unit/ml). The frequency test results indicated that except for the weakest hydrogel sample, G' was independent of the frequencies, indicating rigid and elastic networks. Test results of strain sweeps of HA-Tyr hydrogels indicated that the G' of hydrogels formed with $H_2O_2$ concentrations between 0.146 and 0.437 mM was independent of strain, demonstrating that these hydrogels were physically stable. Above 0.582 mM of $H_2O_2$, the hydrogels showed a slight increase in G' at high strain. Furthermore, the hydrogel formed with 0.728 mM of $H_2O_2$ showed a sudden decrease in G' beyond 60% strain, indicating a yield stress where the hydrogel was deformed irreversibly. The observed yielding is ascribed to the inherent brittle structure of hydrogels possessing high G'.

Example I-C

Swelling Ratio of HA-Tyr Hydrogels

Swelling ratios were determined for slab-shaped HA-Tyr hydrogels. To form the slab-shaped HA-Tyr hydrogels, lyophilized HA-Tyr was dissolved in PBS at a concentration of 1.75 w/v %.

5 µl of a HRP solution with an appropriate concentration was added to 1 ml of HA-Tyr solution to give a final HRP concentration of about 0.124 unit/ml of HRP.

For different samples, 5 µl of different concentrations of $H_2O_2$ solution to give respective final $H_2O_2$ molarity of about 0.160, 0.291, 0.437, 0.582 or 0.728 mM.

Crosslinking of HA-Tyr was initiated by the addition of HRP and $H_2O_2$.

The mixture was vortexed vigorously before it was injected between two parallel glass plates clamped together with 1 mm spacing. The crosslinking reaction was allowed to proceed at 310 K for one hour. Hydrogel slabs were formed.

Round hydrogel disks with diameters of 1.6 cm were cut out from the hydrogel slabs using a circular mold. The hydrogel disks were immersed in PBS at 310 K for 3 days. The swollen disks were then gently blotted dry with Kimwipe and weighed to obtain the swollen weight. The disks were then lyophilized to obtain the dry weight. The swelling ratio is the ratio of the swollen weight to the dry weight.

Figure 5:
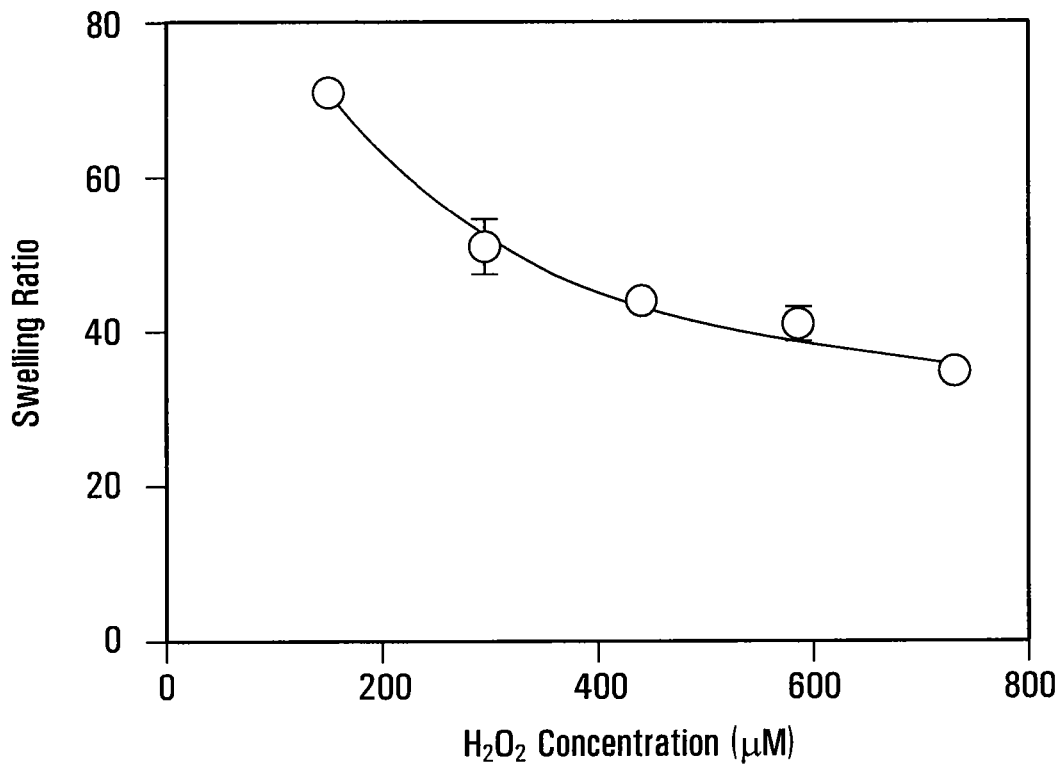

Representative results of measured swelling ratio of sample HA-Tyr hydrogels formed with different concentrations of $H_2O_2$ are shown in FIG. 5. The swelling ratio decreased with increasing concentration of $H_2O_2$, indicating that the swelling capacity was reduced due to increased crosslinking density.

Sample Hydrogels formed with 0.728 mM of $H_2O_2$ were also swollen in PBS for 24 hours to reach a swelling equilibrium and then immersed in different concentrations of hyaluronidase. After incubation for 37 hours in 2.5 unit/ml, 10 hours in 25 unit/ml, or 4 hours in 125 unit/ml of hyaluronidase, the hydrogels were removed from the solution and rinsed extensively with water before swelling in purified water (Milli-Q™ water) for 2 days. Sample hydrogels without exposure to hyaluronidase were used as controls. The swelling ratios were then determined as described above.

Figure 6:
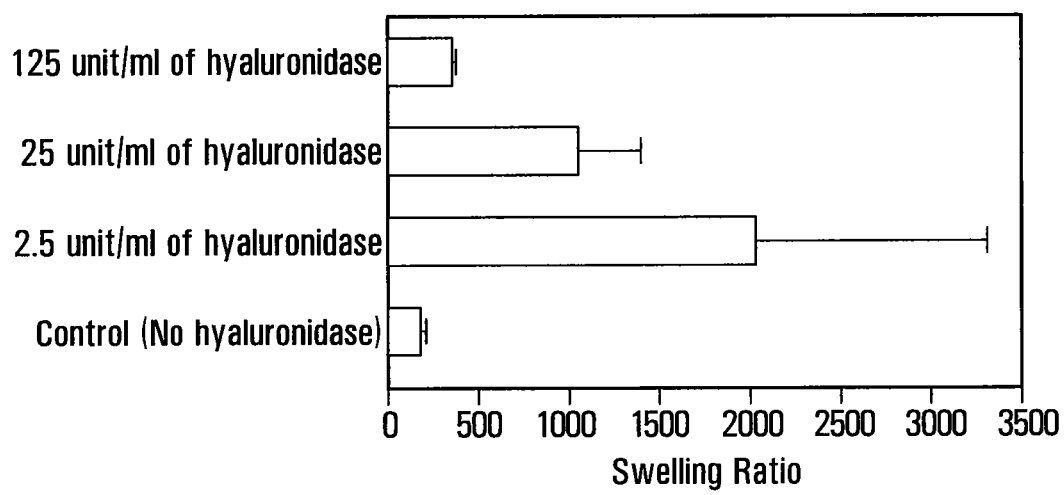
FIG. 6 is a bar graph showing swelling ratio measured from different samples.

Representative measured results are shown in FIG. 6, which shows the measured swelling ratios of sample hydrogels that had lost 50% of their initial weight after incubation at different concentrations of hyaluronidase. The swelling ratios of all sample hydrogels incubated with hyaluronidase were greater than the control sample. This result supports the expectation that the decrease in crosslinking density due to bulk degradation facilitates swelling of the hydrogels during degradation. The swelling ratio increased with decreasing hyaluronidase concentration. This result indicates that bulk degradation occurred in concurrence with surface degradation, which was more dominant at high concentrations of hyaluronidase. However, at low concentrations of hyaluronidase, the effect of surface degradation was diminished, which allowed more time for hyaluronidase to diffuse into the hydrogel network and hence bulk degradation became more predominant.

Example I-D

Morphology Study of HA-Tyr Hydrogels

HA-Tyr hydrogel samples were formed in glass vials with about 0.124 unit/ml of HRP and about 0.437, 0.582 or 0.728 mM of $H_2O_2$. The hydrogel samples were swelled in MilliQ water for 24 hours to reach a swelling equilibrium before being cut into thin slices (2 mm×5 mm×8 mm) using a sharp surgical blade. The samples were frozen rapidly by plunging them into liquid nitrogen slush and then freeze-dried for two days.

Scanning electron microscopy (SEM) images of the lyophilized samples were taken using an FEI Company Quanta™ 200 (Oregon, USA) microscope, which was equipped with a gaseous secondary electron detector, in a low vacuum mode. The SEM images of freeze-dried hydrogel samples revealed that the pore sizes decreased with increasing $H_2O_2$ concentration, which is consistent with the swelling ratio results.

Example I-E

Effects of Gelation Rate on the Subcutaneous Formation of Fluorescent HA-Tyr Hydrogels Nonobese diabetic/severe combined immunodeficiency (NOD/SCID) mice were used immediately after euthanization. After shaving the dorsal sides, each mouse was injected subcutaneously with 0.4 ml of 1.75 w/v % fluorescence-labeled HA-Tyr with 0.728 mM $H_2O_2$ and different concentrations of HRP (0, 0.031 and 0.124 unit/ml). Two hours after injection, the locations of fluorescent HA-Tyr hydrogels were detected using GE's Explore™ Optix fluorescence imaging machine (Waukesha, Wis.) equipped with a 470 nm excitation laser. After fluorescence imaging, incisions were made to expose the site of injections and digital photographs were taken.

Fluorescence images were taken to observe the position of the HA-Tyr hydrogels formed in the mice body. When the HA-Tyr solution was injected without HRP, no gel formation was observed and the injected solution spread out from the administered site, suggesting that the polymer solution diffused readily in the subcutaneous environment. When HRP were added at an increasing concentration from about 0.031 to about 0.124 unit/ml, the surface area showing fluorescence decreased, while the observed fluorescence intensity increased, indicating hydrogel formation was more localized at the injection site, likely due to the faster gelation rate. The hydrogel formed with 0.124 unit/ml of HRP had a better defined 3-dimensional structure, compared to the hydrogel formed with 0.031 unit/ml of HRP.

Example I-F

Enzymatic Degradation of HA-Tyr Hydrogels

Hydrogel disks were prepared as described above and were swollen in PBS for 24 hours to reach the swelling equilibrium. The disks were sandwiched between plastic nets to facilitate retrieval of the hydrogels during degradation experiment. The hydrogels were immersed in 20 ml of PBS containing hyaluronidase (0, 2.5, 25 or 125 unit/ml) at 310 K in an orbital shaker rotating at 100 rpm. The extent of degradation of the hydrogels was estimated by measuring both the residual hydrogel weight and the amount of uronic acid (a degradation component of HA) in the degradation solution at different times. To measure the residual weight, the hydrogels were removed from the degradation solution with a pair of forceps, gently blotted dry with Kimwipe™, and weighed. To measure the amount of uronic acid released from the hydrogel, 0.350 ml of the degradation solution was removed and stored in microcentrifuge tubes at about 277 K until analysis. 0.350 ml of freshly prepared degradation solution were then added to maintain the total volume of 20 ml. Degradation experiments were continued until no visible signs of gel remained. It was determined that the activity of hyaluronidase remained 90 percent for 2 days. The amount of uronic acid released from the hydrogel into the degradation medium were assayed using a carbazole assay. 0.3 ml of samples were added to 1.5 ml of 0.025 M sodium tetraborate in sulfuric acid and heated at 373 K for 10 minutes. After cooling to room temperature, 0.1 ml of carbazole (0.125 w/w % in ethanol) was added, mixed and heated at 373 K for 15 minutes. After cooling to room temperature, 0.2 ml of the solution was transferred to a 96 well plate and the absorbance of the solution was measured at 530 nm. The amount of uronic acid in each sample was estimated by comparing to the D-glucuronic acid standards.

Hydrogel samples formed with a fixed HRP concentration (0.124 unit/ml) but different $H_2O_2$ concentrations (0.437, 0.582, 0.728 mM) were used to study the relationship between mechanical strength and degradation. Degradations of sample HA-Tyr hydrogels were carried out in the presence of 2.5, and 125 unit/ml of hyaluronidase, and analyzed by the measurement of uronic acid production and hydrogel weight loss. Bovine testes hyaluronidase was used as a hydrolytic enzyme.

Test results indicated that degradation did not occur when hyaluronidase was absent. In the presence of hyaluronidase, the degradation rate depended on the mechanical strength of the hydrogel sample: a stronger hydrogel degraded slower than a weaker hydrogel at the same hyaluronidase concentration. Thus, it can be concluded that the degradation rate of HA-Tyr hydrogels may be conveniently adjusted by changing the $H_2O_2$ concentration in the precursor solution.

The weight of the sample hydrogels was also measured at selected time points during the degradation period. At 125 unit/ml of hyaluronidase, the hydrogels lost weight linearly with time, in line with the trend of uronic acid production observed in the carbazole assay, suggesting surface degradation. At lower concentrations (2.5 and 25 unit/ml) of hyaluronidase, the hydrogels swelled (negative weight loss) initially before starting to lose weight (all hydrogel samples were swollen in PBS for 24 hours to reach the swelling equilibrium before degradation). The weakest hydrogel sample (formed with 0.437 mM $H_2O_2$) at the lowest concentration (2.5 unit/ml) of hyaluronidase swelled the most. Based on the shape of the hydrogel samples (slab-shaped) and the observed swelling behavior, it appears that crosslinking density decreased with time due to bulk degradation. The fact that more pronounced bulk degradation was observed in weaker hydrogel samples was expected as a lower crosslinking density could allow faster diffusion of hyaluronidase into the matrix of the hydrogel.

As can be understood, these results show that the mechanical strength of the HA-Tyr hydrogel may be tuned to optimize its degradation profile for different applications.

The HA-Tyr hydrogels formed in these examples were shown to be injectable and biodegradable. It was also found that independent control of mechanical strength and gelation rate could be achieved by limiting the molarity of $H_2O_2$ in the precursor solution low and keeping the HRP concentration above a threshold. At a constant HA-Tyr concentration, G' was varied from 10 to 4000 Pa by increasing $H_2O_2$ concentration while maintaining a constant and rapid gelation rate.

It was also shown that changing the $H_2O_2$ concentration can tune the mechanical strength of the hydrogel and thus achieve fine control of hydrogel degradation rate.

These results also show that rapid gelation could prevent diffusion of injected HA-Tyr polymer solution in the body, thus localizing gelation at the injection site.

Further measurement results and discussions related to Example I are disclosed in Lee.

Example II

Example II-A

Synthesis of HA-Tyr Hydrogels

HA-Tyr conjugates were synthesized as described in Example I. The degree of substitution was 6 as determined by $^1$H NMR.

5 µl of an HRP solution and 5 µl of an $H_2O_2$ solution were added sequentially to an HA-Tyr solution containing 0.24 ml of HA-Tyr conjugate (1.82 w/v %) dissolved in a PBS solvent. The concentrations of the HRP and $H_2O_2$ solutions were selected so that the final concentration of HRP in the resulting HA-Tyr solution was about 0.031 or about 0.124 unit/ml, and the final concentration of $H_2O_2$ were about 0.437, 0.582, or 0.728 mM.

The solution was pre-warmed to a temperature of about 310K. The final concentration of HA-Tyr conjugate in the resulting HA-Tyr solution was about 1.75 w/v %.

The mixture was vortexed immediately after addition of HRP and $H_2O_2$.

0.210 ml of the resulting HA-Tyr solution was applied to the bottom plate of an rheometer. The upper cone was then lowered to a measurement gap of 0.025 mm and a layer of silicon oil was carefully applied around the cone to prevent solvent evaporation. The solution was allowed to form a HA-Tyr hydrogel.

Rheological measurements of the samples were made in the same manner as in Example I-C. For each sample, the measurement continued until the storage modulus of the sample reached a plateau.

Example II-B

Synthesis of Hydrogels Loaded with Protein

BSA or lysozyme was dissolved in PBS to form protein solutions with different concentration. 0.065 ml of each protein solution was added to 0.175 ml of an HA-Tyr conjugate solution (2.5 w/v %). The mixed solution was mixed gently. 5 µl of HRP and 5 µl of $H_2O_2$ were next added to the mixed solution. The final concentration of HA-Tyr conjugate in the resulting solution was about 1.75 w/v % and the protein loading concentrations were 0.15, 1.5 or 15 mg/ml respectively.

The resulting solution was used to form hydrogels as described in Example II-A.

Example II-C

Conjugation of Alexa Fluor 680 Fluorescent Dye to Lysozyme 0.5 mg of amine-reactive Alexa Fluor 680 carboxylic acid succinimidyl ester dissolved in 50 µl DMSO was added to 12.34 mg lysozyme dissolved in 1.5 ml PBS. The mixture was stirred gently at room temperature for 5 hours in darkness. The reaction mixture was passed through PD-10 desalting columns (GE Healthcare) pre-equilibrated with PBS (0.5 ml per column) to remove un-conjugated dyes. The first fluorescent bands containing the labeled proteins were collected and the concentration of proteins in the elution was estimated by bicinchoninic acid protein assay (BCA, Piercer™). The protein conjugate was then diluted to 40 µg/ml and the absorbance of Alexa Fluor 680 at 679 nm was determined using a UV-VIS spectrometer (Hitachi™). The fluorescence to protein (F/P) molar ratio was calculated to be 0.39 according to the manufacturer's instructions.

Example II-D

Subcutaneous Injections of Protein-Loaded HA-Tyr Hydrogels

Fluorescence-labeled HA-Tyr was synthesized as described in Lee. The degree of conjugation (substitution) of aminofluorescein or tyramine was 0.5 or 5, respectively. Immediately after euthanization by $CO_2$, each adult female Balb/c nude mice was injected subcutaneously on its back with 0.3 ml of 1.75 w/v % fluorescence-labeled HA-Tyr solution containing 80 µg of either Alexa 680 conjugated BSA or lysozyme.

About one hour after injection, fluorescence images were taken using the IVIS imaging system (Caliper Life Science™, Massachusetts, USA) to determine the location of HA-Tyr conjugates (GFP filter set, $\lambda_{ex}$=445-490 nm, $\lambda_{em}$=515-575 nm, exposure time=0.05 second) and the proteins (Cy5.5 filter set, $\lambda_{ex}$=615-665 nm, $\lambda_{em}$=695-770 nm, exposure time=0.01 second). For both detections, the binning of the CCD camera was set to 8; field of view (FOV) was 20 cm and the aperture the lens on the camera was set to f/8.

Example II-E

In-Vitro Protein Release from HA-Tyr Hydrogels

HA-Tyr hydrogels loaded with 0.25 mg/ml of α-amylase or lysozyme were prepared by mixing 0.5 ml of HA-Tyr (3.5 w/v %) with 0.5 ml of protein solution (0.5 mg/ml). 5 µl of an HRP solution and 5 µl of an $H_2O_2$ solution was added to form a mixture. The final concentration of HRP in the mixture was about 0.124 unit/ml and the final molarity of $H_2O_2$ in the mixture was about 0.437, 0.582 or 0.728 mM. The mixture was vortexed gently before being deposited (injected) between two parallel glass plates clamped together with 1 mm spacing.

Gelation was allowed to proceed at 310 K for one hour, forming hydrogel slabs. Round gel disks with a diameter of 1.6 cm were cut out from the hydrogel slab using a circular mold. Each disk was sandwiched between a plastic net and immersed in 20 ml of a release medium containing PBS, with or without hyaluronidase (2.5 unit/ml). At various selected time intervals, 0.2 ml of the release medium was drawn and stored in a microcentrifuge tube containing 0.2 ml of 0.1 mg/ml BSA in PBS to prevent non-specific adsorption of the model proteins to the plastic surface of the microcentrifuge tubes. 0.2 ml of a PBS solution with or without hyaluronidase was added to maintain the total release medium at 20 ml. The collected samples were stored at about 253 K.

The amount of proteins contained in each sample was determined by enzyme-linked immunosorbant assay (ELISA) which was carried out at room temperature. The washing procedure between each steps was carried out using a plate washer (Amersham Bioscience™) which was programmed to wash the wells three times with 0.3 ml washing buffer (100 mM PBS containing 0.05% Tween-20). 0.1 ml of each sample solution thawed to room temperature was added to the wells of a 96-well MaxiSorb™ ELISA plate (NUNC™) and the proteins in the samples were bound to the well by incubation for 1.5 hours and then the wells were washed. After washing, the wells were blocked with 0.2 ml of blocking buffer (BSA 2 w/v % in PBS) for 30 minutes to saturate the protein-binding sites and then the wells were washed. Next, 0.1 ml of either biotinylated anti-α-amylase (2 µg/ml) or anti-lysozyme (1.67 µg/ml) antibodies diluted in blocking buffer were added to the wells and incubated for 1 hour. After washing, 0.1 ml of streptavidin-alkaline phosphatase diluted in PBS was added and incubated for 1 hour and then the wells were washed. Finally, 0.1 ml of p-NPP was added to each well and the plate was incubated until sufficient color had developed (approximately 80 min for α-amylase and 35 min for lysozyme). The absorbance at 405 nm was measured using Tecan Infinite™ 200 microplate reader. The amount of proteins contained in each sample was calculated by comparing with a set of protein standards and was converted to percentage of total protein encapsulated in the hydrogel disk. It was observed that the ELISA signal of a solution of α-amylase in PBS (2.66 µg/ml) at 310 K decreased linearly with time and was reduced by 30% after 24 hours. This might due to adsorption of α-amylase to glass surface or denaturation of the protein. In order to compensate for the loss in signal, the amount of proteins detected by ELISA was manually offset according to the percentage loss observed in the controls.

Example II-F

Protein Release in Different Ionic Strengths

Hydrogel disks (thickness=1 mm, weight=57 mg) containing 0.25 mg/ml of lysozyme were immersed in 1 ml of NaCl solution (0, 0.05, 0.15, 0.5 or 1 M) at 310 K on an orbital shaker at 100 rpm. After four hours of incubation, 0.1 ml of the release medium was collected and the amount of proteins contained in the sample was measured using the micro bicinchoninic acid protein assay (microBCA, Pierce) according to the manufacturer's protocol.

Example II-G

Activities of Proteins Recovered by Degradation of HA-Tyr Hydrogels

Hydrogel disks (thickness=1 mm, weight=57 mg) containing 5 mg/ml of α-amylase or lysozyme were degraded in 5 ml of 200 unit/ml of hyaluronidase in PBS (supplemented with 0.05% $NaN_3$) at 310 K on an orbital shaker at 150 rpm. After 24 hours, no visible sign of an hydrogel was observed. The activity of α-amylase was determined by EnzChek™ Ultra Amylase Assay Kit (Invitrogen™).

The degradation solutions containing the released α-amylase were diluted 200-folds with PBS. 50 µl of the diluted samples were added to the wells of a 96 well fluorescent plate and then 50 µl of the substrates were added. The plate was incubated for 10 minutes on an orbital shaker at room temperature and then the fluorescence intensity ($\lambda_{ex}$=485 nm, $\lambda_{em}$=530 nm) was measured using the Tecan Infinite 200 microplate reader. To determine the activities of lysozyme, 20 µl of lysozyme samples was added to the well of a 96-well UV-starplate (Greiner Bio-one™, Germany) followed by 0.1 ml of *Micrococcus lysodeikticus* (0.15 w/v % in PBS). The plate was incubated for 15 minutes on an orbital shaker at 50 rpm at room temperature. Then the absorbance at 450 nm was measured using the microplate reader.

It was found from the test results that it is desirable at least in some applications for the hydrogel to form (crosslink) rapidly. It was found that slow gelation could cause diffusions of the gel precursors and the proteins to be encapsulated in tissues surrounding the injection site, which could compromise the therapeutic outcome.

It was also found that from the tests that about 0.124 unit/ml of HRP was the highest concentration suitable for injection of a 0.3 ml HA-Tyr conjugate solution without clogging of the needle that was used. It should be understood, however, in other applications, the suitable maximum of [HRP] may be higher or lower.

It was further found from these tests that in the absence of HRP, no crosslinked network was formed and both the HA-Tyr and the proteins diffused away from the injection site, suggesting that both components diffused readily in the subcutaneous environment. Notably, the area detected with proteins were greater than the area detected with HA-Tyr, indicating that the proteins diffuse faster than HA-Tyr conjugate, likely due to the smaller molecular weight of BSA (BSA 66 kDa and HA 90 kDa).

At about 0.031 unit/ml of HRP, the area detected with HA-Tyr did not reduce, suggesting that the crosslinking reaction was not quick enough to confine the crosslinked network at the injection site. However, the area detected with proteins decreased slightly, indicating that crosslinking of the HA-Tyr conjugates helped trapping the proteins within the network.

By increasing the HRP concentration to 0.124 unit/ml, both the surface areas detected with HA-Tyr and proteins were significantly reduced, indicating that the rapid gelation resulted in localized formation of the hydrogels and effective encapsulation of the proteins within the network.

As can be appreciated, rapid gelation may be desirable for an injectable hydrogel system to ensure that the delivery would be localized to the site of injection.

Test results also showed that when the concentrations of HA-Tyr conjugate and HRP were fixed, the storage modulus (G') of the hydrogel, which was related to the crosslinking density, increased with $H_2O_2$ concentration. Some results are listed in Table III (See samples 2-4).

It was found that when BSA was included in the precursor solution and encapsulated in the hydrogel, G' decreased by about 7%, indicating that the network integrity was slightly affected by the presence of BSA (Table III, samples 5-7).

Encapsulating lysozyme at 15 mg/ml showed a marked decrease in G' (Table III, sample 10). This is likely due to the electrostatic interactions between the negatively-charged HA and the positively-charged lysozymes which interfered with the crosslinking reaction (more discussions about the electrostatic interactions in Section 3.3). However, the gel points of the hydrogels formed with same HRP concentration (0.124 unit/ml), with or without proteins were all less than 90 seconds, indicating that protein encapsulation did not affect the rate of enzymatic crosslinking.

The release of α-amylase from HA-Tyr hydrogels, regardless of its crosslinking density, exhibited a burst release which was expected primarily due to the protein concentration gradient inside and outside of the hydrogel that caused the proteins near the surface of the gel to diffuse rapidly out of the matrix. The percentage of proteins released during the burst phase decreased as the crosslinking density increased. After the burst release, the release of α-amylase slowed down.

The release profile of lysozymes displayed a similar burst release which decreased with increasing crosslinking density. However, for hydrogels with the same crosslinking density, the percentage of lysozyme released in the burst phase was much lower than that of α-amylase. Furthermore, the release of lysozymes from HA-Tyr hydrogels discontinued after the burst release.

It is desirable that a hydrogel system for protein delivery not only delivers the protein at a controlled rate but also maintains the activity of the protein from the time of hydrogel preparation to the point of release. In addition, degraded products from the delivery system might cause protein denaturation. Therefore, it may be desirable that the gel-forming process and the degraded products of the hydrogel system maintains the activity of the protein at the therapeutic level.

TABLE III

Representative test results obtained from sample hydrogels

| Sample | HRP (unit/ml) | $H_2O_2$ (mM) | Encapsulated Protein Name | Loading (mg/ml) | Storage Modulus G' (Pa) | Gel Point (s) |
|---|---|---|---|---|---|---|
| 1 | 0.031 | 0.728 | — | — | 1997 ± 101 | 371 ± 28 |
| 2 | 0.124 | 0.437 | — | — | 893 ± 109 | 78 ± 3 |
| 3 | 0.124 | 0.582 | — | — | 1739 ± 221 | 82 ± 1 |
| 4 | 0.124 | 0.728 | — | — | 3139 ± 43 | 71 ± 16 |
| 5 | 0.124 | 0.728 | BSA | 0.15 | 2704 ± 49 | 60 ± 26 |
| 6 | 0.124 | 0.728 | BSA | 1.5 | 2909 ± 155 | 77 ± 2 |
| 7 | 0.124 | 0.728 | BSA | 15 | 2911 ± 267 | 69 ± 3 |
| 8 | 0.124 | 0.728 | Lysozyme | 0.15 | 3001 ± 72 | 68 ± 14 |
| 9 | 0.124 | 0.728 | Lysozyme | 1.5 | 2914 ± 94 | 90 ± 15 |
| 10 | 0.124 | 0.728 | Lysozyme | 15 | 2575 ± 186 | 85 ± 6 |

In summary, the test results described in Example II show that localized hydrogel formation and efficient encapsulation of proteins could be achieved by rapid gelation of HA-Tyr hydrogels using a high concentration of HRP. Sustained release of negatively-charged α-amylase at different release rates could be achieved by varying the $H_2O_2$ concentration in the precursor solution. The activity of released α-amylase remained above 95% at different hydrogel crosslinking densities. Sustained release of positively-charged lysozymes was observed only when the hydrogel network was degraded. The activity of the released lysozymes depended on the crosslinking density of the hydrogel, but the minimum activity was 70%. These results showed that the sample hydrogels were suitable for use in an injectable system for sustained release or delivery of proteins or other like materials.

As illustrated by Examples I and II, including the rheological data, swelling ratio studies and morphological analysis demonstrated that, when the $H_2O_2$ concentration in the precursor solution was limited to a low range, variation of $H_2O_2$ concentration effectively controlled the mechanical strength of the formed hydrogel without substantially affecting the gelation rate. Further, variation of the HRP concentration effectively controlled the gelation rate in the gelation process without substantially affecting the mechanical strength of the formed HA-Tyr hydrogel when the HRP concentration is above a certain threshold. Thus, independent control of gelation rate and mechanical strength (crosslinking density) were conveniently obtained.

As now can be understood, embodiments of the present invention enables convenient control of the hydrogel crosslinking density and gelation rate/speed. The degradability of the resulting hydrogel and the release rate of protein or drug or another material embedded in the hydrogel may be conveniently controlled by varying the $H_2O_2$ concentration in the precursor solution.

Thus, embodiments of the present invention may be advantageously used in many different fields and applications including drug or protein delivery and tissue engineering applications.

Example III

Gtn-HPA Conjugate

Figure 7:
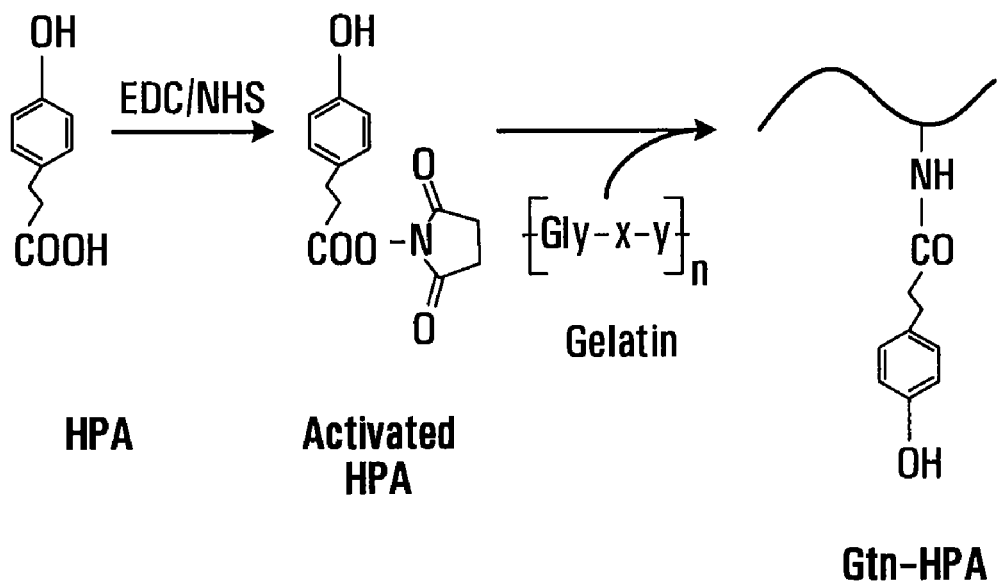
FIG. 7 is a schematic chemical formula of a reaction route for forming Gtn-HPA conjugate.

Samples of Gtn-HPA conjugates were prepared in a carbodiimide ester-mediated coupling reaction process as illustrated in FIG. 7.

A solvent mixture of distilled water and dimethylformamide (DMF) was prepared, with the weight ratio of distilled water to DMF being 3:2 in the mixture.

3.32 g of HPA (20 mmol), 3.2 g of NHS (8 mmol) and 3.82 g of EDC-HCl (20 mmol) were dissolved in 250 ml of the above solvent mixture to form a first solution. The first solution was stirred at room temperature for about five hours, while the pH of the solution was maintained at about 4.7, by adding an acid (HCl) or a base (NaOH).

An aqueous Gtn solution containing about 6.25 wt % of Gtn was prepared. 150 ml of the Gtn solution was added to the first solution after about five hours to form a second solution. The second solution was stirred over night at room temperature at pH of about 4.7.

In the first and second solutions, the reactions shown in FIG. 7 occurred respectively, thus forming Gtn-HPA conjugate in the resulting second solution.

The resulting second solution was transferred to dialysis tubes with molecular cut-off at 1000 Da. The solution in the tubes was dialyzed against 100 mM of a sodium chloride solution for two days, a mixture of distilled water and ethanol (with water to ethanol volume ratio of 3:1) for one day, and distilled water for one day, successively, to form a purified solution.

The purified solution was lyophilized to obtain sample Gtn-HPA conjugate (Sample 11).

The overall yield of Gtn-HPA was about 78 to about 83%.

The degree of HPA substitution was determined according to the conventional TNBS technique discussed above, and was found to be 13, i.e. there were 13 HPA molecules present per 100 amino-acid residues of Gtn. About 90% of the amine groups in Gtn were conjugated with HPA.

The ingredients and measurement results for Sample 11 are summarized in TABLE IV.

TABLE IV

| Sample 11 (Gtn-HPA conjugate) | | | | |
|---|---|---|---|---|
| | Gtn | EDC-HCl | NHS | HPA |
| Contents of precursor solution (g) | 10 | 3.82 | 3.20 | 3.32 |
| Yield (g) | | 6.84 | | |
| Degree of Substitution | | 13 | | |

Example IV

Gtn-HPA-Tyr Conjugate

Figure 8:
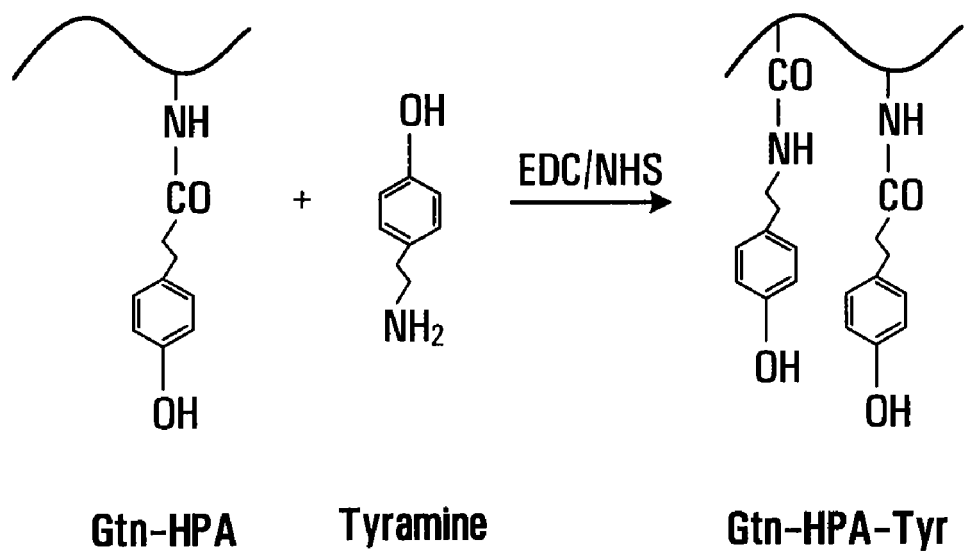
FIG. 8 is a schematic chemical formula of a reaction route for forming Gtn-HPA-Tyr conjugate.

Samples of Gtn-HPA-Tyr conjugates were prepared in a two-step reaction route as illustrated in FIGS. 7 and 8.

The first step was as described above in Example III up to the point of obtaining the purified solution (also see FIG. 7).

In the second step, Tyr, NHS, and EDC-HCl were added to the purified Gtn-HPA solution. The concentrations of respective materials in the precursor solutions for two different samples are shown in at TABLES V and VI. The resulting solutions were stirred overnight at pH of about 4.7 pH. The purifying and lyophilization procedures described in Example were performed with these solutions to obtain sample Gtn-HPA-Tyr conjugates. Two samples, Sample 12 and Sample 13 were obtained (see TABLES V and VI).

In this case, the degree of substitution was calculated from $^1$H NMR measurement by comparing the ratio of relative peak integrations of aromatic protons in HPA or Tyr ($\delta$=7.3 ppm) and aromatic protons in phenylalanine and tyrosine residues in gelatin ($\delta$=7.1 or 6.8 ppm respectively).

Figure 9:
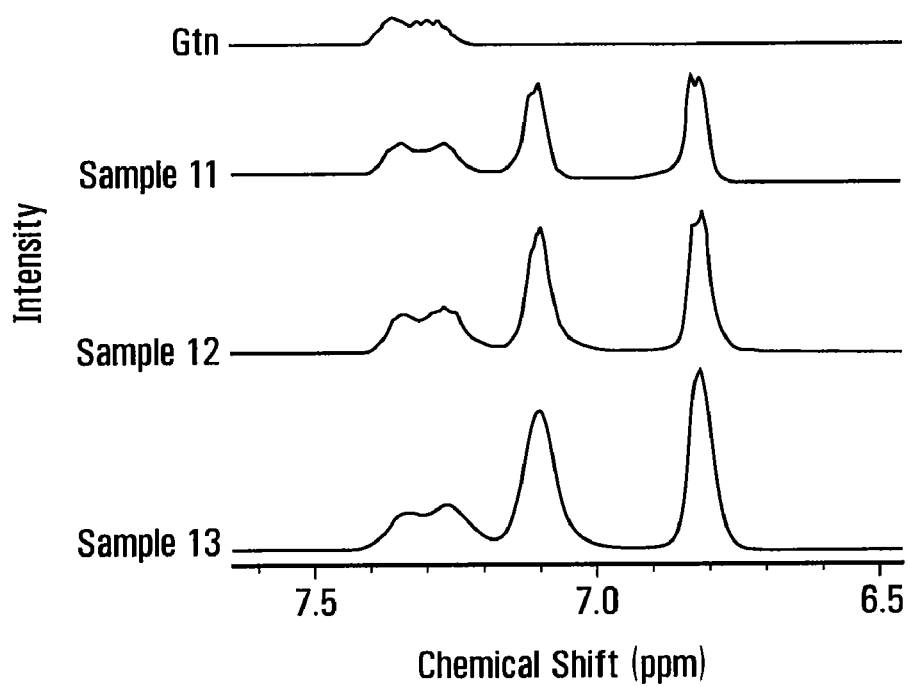
FIG. 9 is a line graph of measured proton nuclear magnetic resonance ($^1$H NMR) spectra of sample compounds.
Figure 10:
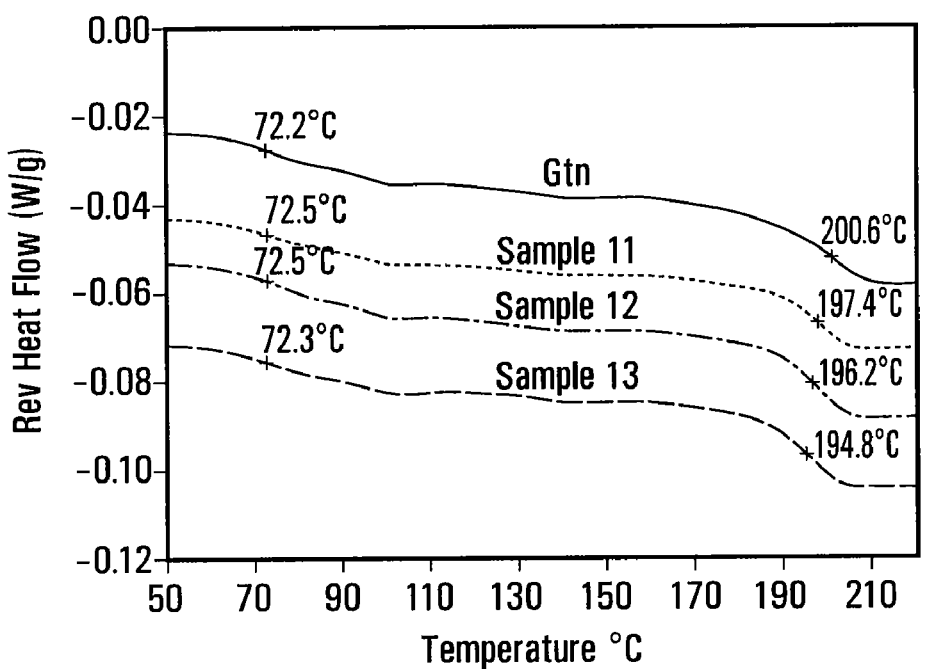
FIG. 10 is a line graph of differential scanning calorimeter (DSC) measurements of the sample compounds.

FIG. 9 shows representative comparison results of the $^1$H NMR measurement from the samples.

The total number of HPA and Tyr molecules conjugated to Gtn in the sample conjugate was 16 and 21 for Samples 12 and 13 respectively.

The measurement results for Samples 12 and 13 are summarized in TABLES V and VI respectively.

TABLE V

Sample 12 (Gtn-HPA-Tyr conjugate)

|  | Gtn-HPA | EDC-HCl | NHS | Tyr |
|---|---|---|---|---|
| Contents of precursor solution (g) | 6.84 | 0.1265 | 0.1056 | 0.275 |
| Yield (g) |  | 7.13 |  |  |
| Degree of Substitution (%) |  | 16 |  |  |

TABLE VI

Sample 13 (Gtn-HPA-Tyr conjugate)

|  | Gtn-HPA | EDC-HCl | NHS | Tyr |
|---|---|---|---|---|
| Contents of precursor solution (g) | 6.84 | 0.1584 | 0.1320 | 0.550 |
| Yield (g) |  | 7.24 |  |  |
| Degree of Substitution (%) |  | 16 |  |  |

Example V

Thermograms of Gtn, and Samples 11, 12 and 13 were recorded using a differential scanning calorimeter (DSC Q100, TA Instruments™) to heat the samples (6 mg each) in a crimped standard aluminum pans from 35° C. to 220° C. at an incremental rate of 10° C./min. Representative DSC results are shown in FIG. 4. As can be seen, the second glass transition temperature of Gtn was different in different samples, decreasing with increasing degree of phenol substitution. This indicated that the degree of hydrogen bonding in the conjugates was reduced by the phenol substitution.

Example VI

Hydrogel Formation

Aqueous solutions of Samples 11, 12 and 13 were respectively prepared. For each conjugate sample, sample solutions with both 5 wt % and 10 wt % of the conjugate were prepared.

A solution of HRP and a solution of $H_2O_2$ were sequentially added to 250 µl of each conjugate solution. The HRP solutions had the same HRP concentration. Different $H_2O_2$ solutions with different $H_2O_2$ concentrations were used to study the effect of variation in $H_2O_2$ concentration alone. The $H_2O_2$ concentration in the final precursor solution was varied from 0.1 mM to 20 mM. The HRP concentration in the final precursor solution was about 0.15 units/ml.

The precursor solutions were mixed and allowed to react at a temperature of about 37° C. Hydrogels were formed after about 30 seconds.

Rheological measurements of the hydrogel formation were performed with a HAAKE Rheoscope 1 rheometer (Karlsruhe™, Germany) using a cone and plate geometry of 35 mm diameter and 0.945° cone angle. The measurements were taken at 37° C. in the dynamic oscillatory mode with a constant deformation of 1% and frequency of 1 Hz. To avoid slippage of samples during the measurement, a roughened glass bottom plate was used. Each precursor solution was vortexed and then immediately applied to the bottom plate. The upper cone was then lowered to a measurement gap of 0.024 mm and a layer of silicon oil was carefully applied around the cone to prevent solvent evaporation during measurement. The measurement continued until the measured storage modulus (G') reached a plateau, which indicated that crosslinking had been completed.

Figure 11:
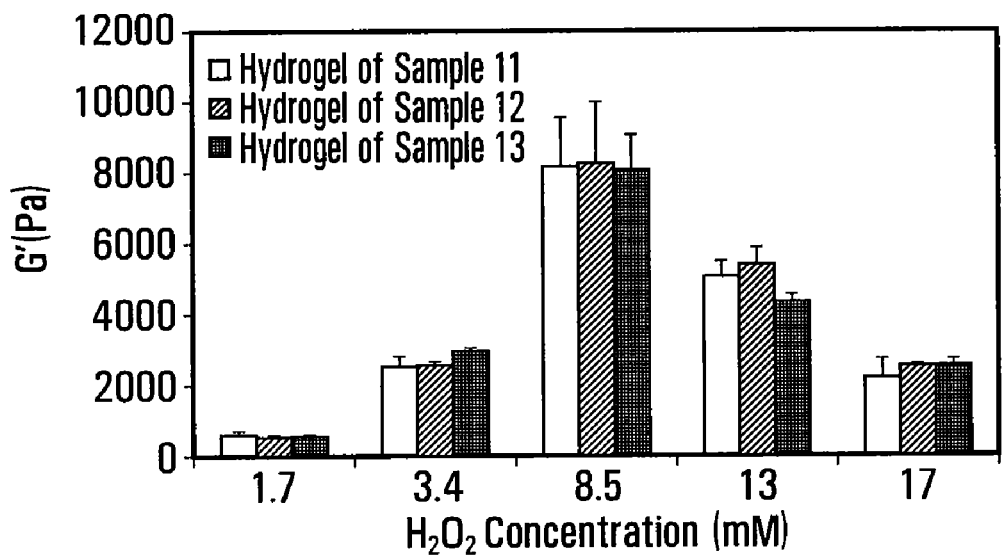
FIG. 11 is a bar graph of measured storage modulus of the sample hydrogels formed from different precursor solutions with different $H_2O_2$ concentrations and 5 wt % of Gtn-phenol conjugate.
Figure 12:
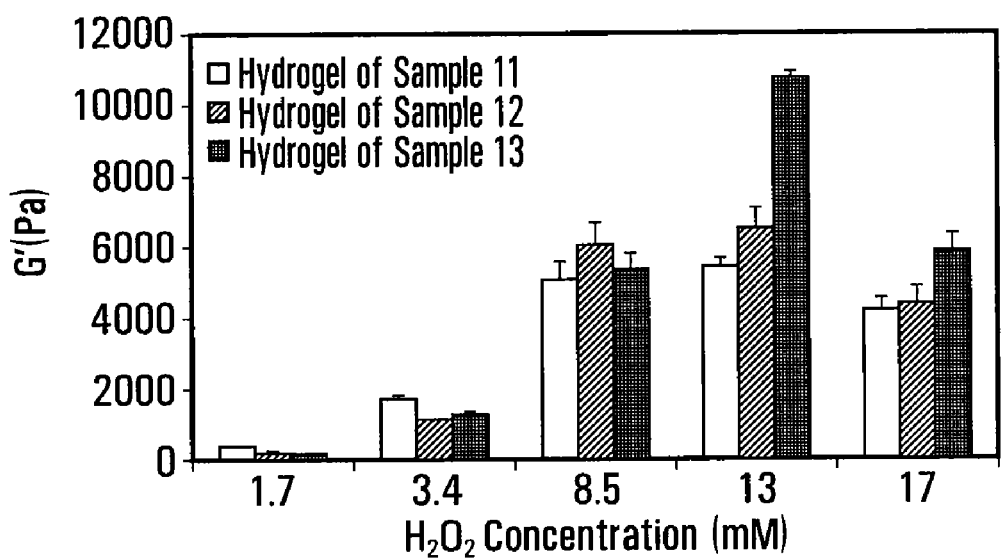
FIG. 12 is a bar graph of measured storage modulus of the sample hydrogels formed from different precursor solutions with different $H_2O_2$ concentrations and 10 wt % of Gtn-phenol conjugate.

Representative measurement results of sample hydrogels formed from samples 11, 12 and 13 are shown in FIG. 11 (with 5 wt % of conjugate in the precursor solution) and 12 (with 10 wt % of conjugate). As shown in FIG. 11, G' varied in the range from about 500 to about 8000 Pa, and was maximized at 8.5 mM of $H_2O_2$ concentration. G' was lower when the $H_2O_2$ concentration was either reduced to below 8.5 mM or increased to above about 13 mM. The decrease in G' at higher $H_2O_2$ concentration is likely due to HRP deactivation of HRP by $H_2O_2$. As shown in FIG. 12, a maximum G' was also observed in the range of $H_2O_2$ concentrations tested, but was shifted to a higher concentration at about 13 mM. Further, significantly, the maximum G' of the hydrogel formed from Sample 3 (with highest Tyr content in the conjugate) was significantly higher than the maximum G' of other sample hydrogels.

As can be seen, the mechanical strength (G') of the sample hydrogels were dependent on the type of the conjugate and the $H_2O_2$ concentration in the precursor solution, and were varied from about 500 to about 27000 Pa.

Some representative results of G' measurements for different hydrogel samples are listed in TABLES VII, VIII and IX respectively. The concentrations of the ingredients in the tables refer to those in the precursor solutions for forming the respective sample hydrogels.

TABLE VII

Hydrogels formed from Sample 11

| Hydrogel | Sample 11 (wt %) | [HRP] (units/ml) | $H_2O_2$ (mM) | G' (Pa) |
|---|---|---|---|---|
| Sample 14 | 5 | 0.15 | 1.7 | 629 ± 71 |
| Sample 15 | 5 | 0.15 | 3.4 | 2529 ± 290 |
| Sample 16 | 5 | 0.15 | 8.5 | 8172 ± 1338 |
| Sample 17 | 5 | 0.15 | 12.8 | 5072 ± 428 |
| Sample 18 | 5 | 0.15 | 17 | 2218 ± 478 |
| Sample 19 | 10 | 0.15 | 1.7 | 998 ± 14 |
| Sample 20 | 10 | 0.15 | 3.4 | 4374 ± 199 |
| Sample 21 | 10 | 0.15 | 8.5 | 12713 ± 1219 |
| Sample 22 | 10 | 0.15 | 12.8 | 13557 ± 665 |
| Sample 23 | 10 | 0.15 | 17 | 10600 ± 810 |

TABLE VII-continued

Hydrogels formed from Sample 11

| Hydrogel | Sample 11 (wt %) | [HRP] (units/ml) | $H_2O_2$ (mM) | G' (Pa) |
|---|---|---|---|---|
| SAMPLE 24 | 1 | 0.15 | 0.85 | 195 ± 25 |
| SAMPLE 25 | 2 | 0.15 | 0.85 | 281 ± 19 |
| SAMPLE 26 | 1 | 0.15 | 1.7 | 258 ± 31 |
| SAMPLE 27 | 2 | 0.15 | 1.7 | 841 ± 45 |

TABLE VIII

Hydrogels formed from Sample 12

| Hydrogel | Sample 12 (wt %) | [HRP] (units/ml) | $H_2O_2$ (mM) | G' (Pa) |
|---|---|---|---|---|
| Sample 28 | 5 | 0.15 | 1.7 | 573 ± 17 |
| Sample 29 | 5 | 0.15 | 3.4 | 2673 ± 104 |
| Sample 30 | 5 | 0.15 | 8.5 | 8517 ± 1745 |
| Sample 31 | 5 | 0.15 | 12.8 | 5144 ± 437 |
| Sample 32 | 5 | 0.15 | 17 | 2590 ± 51 |
| Sample 33 | 10 | 0.15 | 1.7 | 623 ± 34 |
| Sample 34 | 10 | 0.15 | 3.4 | 2874 ± 82 |
| Sample 35 | 10 | 0.15 | 8.5 | 15070 ± 1568 |
| Sample 36 | 10 | 0.15 | 12.8 | 16377 ± 1346 |
| Sample 37 | 10 | 0.15 | 17 | 11063 ± 1157 |

TABLE IX

Hydrogels formed from Sample 13

| Hydrogel | Sample 13 (wt %) | [HRP] (units/ml) | $H_2O_2$ (mM) | G' (Pa) |
|---|---|---|---|---|
| Sample 38 | 5 | 0.15 | 1.7 | 586 ± 17 |
| Sample 39 | 5 | 0.15 | 3.4 | 2952 ± 74 |
| Sample 40 | 5 | 0.15 | 8.5 | 8073 ± 957 |
| Sample 41 | 5 | 0.15 | 12.8 | 4294 ± 255 |
| Sample 42 | 5 | 0.15 | 17 | 2536 ± 170 |
| Sample 43 | 10 | 0.15 | 1.7 | 595 ± 24 |
| Sample 44 | 10 | 0.15 | 3.4 | 3285 ± 122 |
| Sample 45 | 10 | 0.15 | 8.5 | 13507 ± 967 |
| Sample 46 | 10 | 0.15 | 12.8 | 2683 ± 471 |
| Sample 47 | 10 | 0.15 | 17 | 14633 ± 1332 |

Example VII

Enzymatic Degradation of Gtn-Phenol Hydrogels

Sample hydrogels were formed as described in Example VIII. The samples were shaped into disk-shaped slabs with 20 mm diameter and 1 mm thickness. The sample slabs were swollen in PBS for 24 hours and were then sandwiched between plastic nets to facilitate retrieval of the hydrogels from the medium during the degradation tests. The sample hydrogels were immersed in 20 ml of PBS containing 6.1 units/ml of type I collagenase at 37° C. The vials were incubated at 37° C. in an orbital shaker at 100 rpm. The degree of hydrogel degradation was estimated by measuring the hydrogel weight loss. To measure the residual weight, the hydrogels were removed from the solutions, blotted dry and weighed at specific selected time intervals. The degradation tests continued until no gel remained visible.

Figure 13:
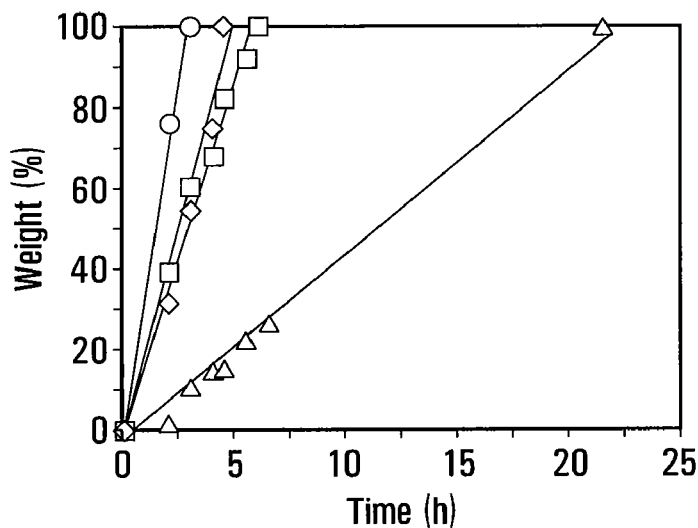
FIGS. 13, 14 and 15 are line graphs of measured hydrogel weight loss as function of time for different sample hydrogels.
Figure 14:
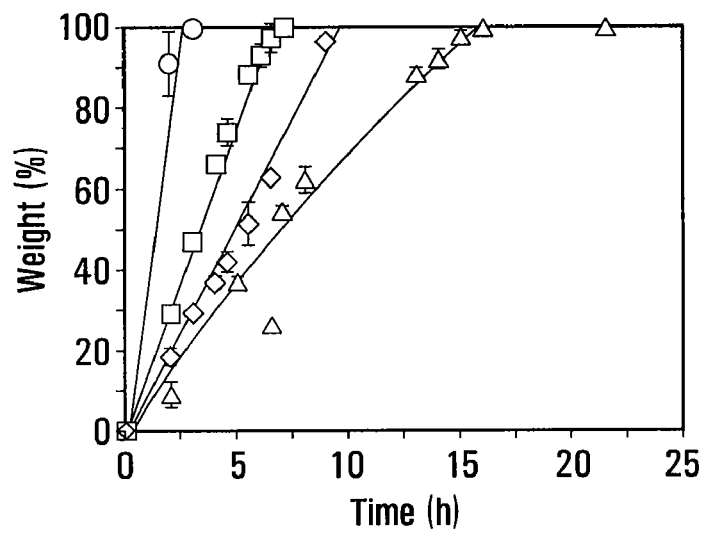
Figure 15:
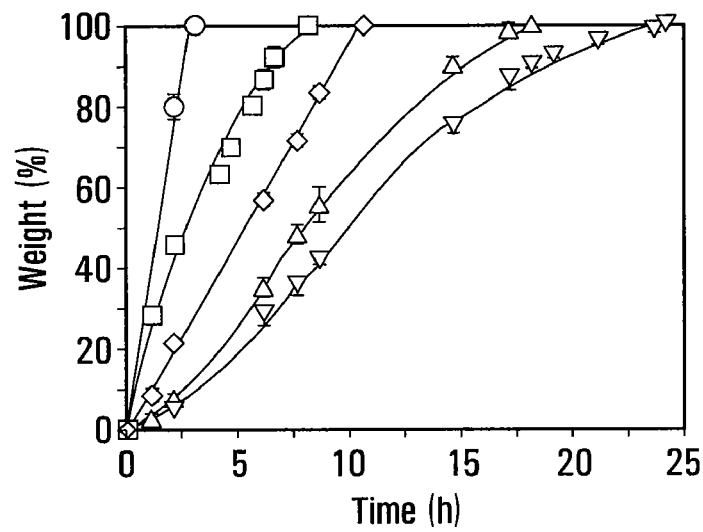

It was found that all sample hydrogels degraded in the presence of collagenase. There was little degradation in the absence of collagenase. FIGS. 13, 14, and 15 show representative degradation profiles of sample hydrogels. The results shown in FIG. 13 were measured from Samples 14 (circle), 15 (square), 16 (triangle) and 18 (diamond). The results shown in FIG. 14 were from Samples 19 (circle), 20 (triangle), 21 (square), and 23 (diamond). The results shown in FIG. 15 were from Samples 43 (circle), 44 (square), 45 (triangle), 46 (reverse triangle), and 47 (diamond). The degradability of each sample correlated strongly with its mechanical strength (see TABLES VII and IX). The degradation rate of the sample hydrogel decreased with increasing mechanical strength.

Example VIII

Cell Culture on Sample Hydrogels

Human mesenchymal stem cells (hMSCs, Cambrex Bio Science Walkersville, Inc., USA) were cultured in mesencult human basal medium supplemented with mesencult human supplement (Stemcell Technologies, Canada). All cells were used at low passage number (p<6). Cells were incubated at 37° C. and 5% $CO_2$. The culture medium was changed every 2-3 days. For studies involving cell differentiation in/on the hydrogels, the cells were pre-treated with mitomycin C (10 µg/ml) for 2 hr to inhibit proliferation and washed three times with culture medium prior to plating.

Hydrogels with different stiffness were prepared in a 24-well plate, according to the procedure described in Example IV. 500 ml of the hydrogel precursor solution was deposited in each well. Hydrogels were formed and allowed to set for 4 hours at 37° C. before incubation in 500 µl of the cell culture medium.

After 12 hours of incubation, the culture medium was removed and 100 µl of cell suspension (with cell density of $1 \times 10^5$ cells/ml) was added to each well. The culture medium was refreshed every 2-3 days.

For proliferation study, the hydrogels were digested using collagenase solution (6.6 unit/ml) at selected time intervals and centrifuged at 1200 rpm. The cultured cells were collected and subjected to lyses. The number of cells on each hydrogel sample was determined by Pico Green assay.

For cell differentiation study, the cultured cells were maintained on the hydrogels for two weeks before immunofluorescence staining.

Cells cultured on the sample hydrogels with different stiffness were stained with lineage-specific antibodies: neurogenesis with neurofilament light chain (NFL, sigma), nestin (Chemicon, USA), microtubule associated protein 2 (MAP2, Chemicon) and 133 tubulin (Sigma) along with desmin (Sigma). Myogenesis with myogenesis differentiation protein 1 (MyoD1, Chemicon) and desmin. Cells were fixed, blocked, permeabilized, and labeled with primary, secondary antibodies and DAPI (Invitrogen, Singapore). Briefly, prior to immunostaining, cells were fixed with 4% formaldehyde solution at room temperature for 20 min and washed three times with phosphate buffer solution (PBS). Permeabilization was carried out using 0.5% Triton X100 in PBS at room temperature for 5 min. The cells were then blocked in 1% bovine serum albumin (BSA) in 0.05% Triton X-100 at room temperature for 1 h. Primary antibody was diluted according to manufacture's recommendation in blocking buffer solution and incubated with the cells at 4° C. overnight. The cells were washed three times with PBS before fluorophore-conjugated secondary antibodies (Invitrogen, Singapore) in blocking buffer were added and incubated in the dark for 30 min. The cell nuclei were counterstained with DAPI (1:15, 000 in water of 5 mg/ml stock) after washing three times with PBS. Fluorescently labeled cells were examined on a confocal laser scanning microscopy (Olympus FV300).

Figure 16:
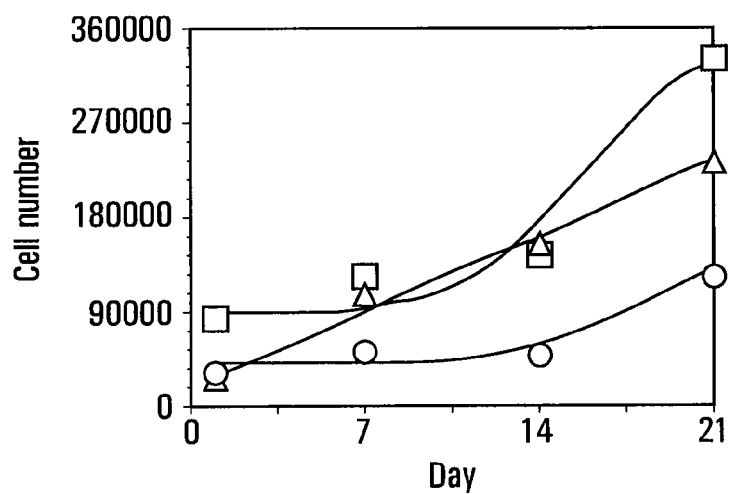
FIG. 16 is a line graph of cell growth over time on sample hydrogel surfaces.

As shown in TABLE VII, the stiffness of the sample hydrogels formed of Sample 11 conjugates initially increased with increasing $H_2O_2$ concentration in the precursor solution, from about 629 to about 8172 Pa when $[H_2O_2]$ increased from 1.7 to 8.5 mM. FIG. 16 shows the time dependence of the total number of cells on the surfaces of Samples 14 (circle), 15 (triangle), and 16 (square). As can be seen, proliferation of hMSCs on the hydrogel surface was dependent on the hydrogel stiffness. It was also observed that while the cell number increased with incubation time on all tested samples, the growth rate increased significantly with increased hydrogel stiffness.

Example IX

Gtn-HPA Hydrogels with hMSC Cells

A conjugate solution was prepared as described in Example VI. Cells were suspended in the solution with a cell density of $1 \times 10^5$ cells/ml. Predetermined amounts of $H_2O_2$ and HRP were then added to different portions of the solution to form precursor solutions. Hydrogels were formed from the precursor solutions and allowed to set for 4 hours, and then immersed in an hMSC culture medium. The culture medium was refreshed regularly. The cells were cultured for two weeks. The cultured cells were incubated with 2 μM Calcein acetoxymethyl ester (Calcein AM, Invitrogen™, Singapore) for one hour at 37° C. and then imaged using confocal laser scanning microscopy (Olympus FV300) to assess 3D projection of the cells.

The same immunostaining protocol as mentioned above was followed to examine fluorescently labeled cells inside the hydrogels. From the immunofluorescence measurements, it was found that cells on both Samples 4 and 5 showed expression of neuron-specific marker 133 tubulin, neurofilament heavy chain (NFH) and neuronal commitment protein marker (nestin), but not cells on Sample 6, which had the highest stiffness. In contrast, MyoD1, myogenesis differentiation protein 1, was expressed in cells on Sample 6. As can be appreciated, the differentiation of hMSC on the Gtn-HPA hydrogel can be controlled by varying the hydrogel stiffness. For example, Gtn-HPA hydrogels with a stiffness of less than about 2530 Pa induced the hMSC to neuronal but Gtn-HPA hydrogels with a stiffness of about 8172 Pa induced the hMSC to muscle cells.

Samples 24, 25, 26 and 27 (see TABLE VII), which were soft hydrogels with G' less than 1000 Pa, were used to assess the hMSC neurogenesis in 3D. It was observed that the cells were adhered and interconnected in 3D in the sample hydrogels. The vast majority of hMSCs were observed with branched and filopodia-rich morphology after one week of culture inside the hydrogels. After two weeks of culture, the cells showed positive staining for NFH, NFL, in tubulin and microtubule Associated protein 2 (MAP2).

Example X

Cell growth and proliferation in two sample Gtn-HPA hydrogels with different stiffness were monitored.

Figure 17:
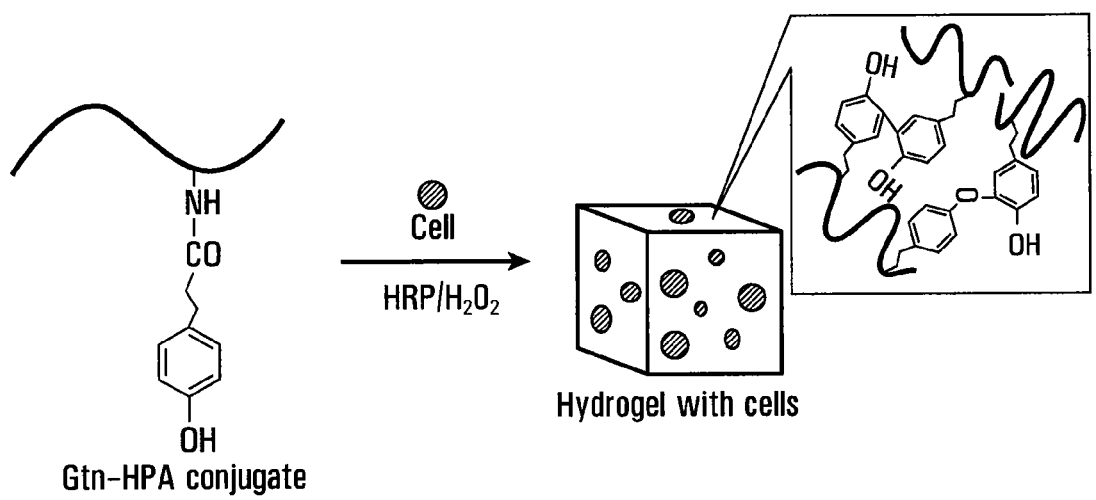
FIG. 17 is a schematic diagram illustrating a route for forming a hydrogel with cells cultured therein.

The sample hydrogels were formed according to the procedure described in Examples IV and VI except that the Gtn-HPA conjugate used in the precursor solutions was 2 wt % for both samples, and cells were dispersed in the precursor solutions as illustrated in FIG. 17. As schematically depicted in FIG. 17, the cells were grown within the sample hydrogel, and the polymer matrix in the hydrogel was formed of conjugates that were crosslinked through the phenol groups. The $H_2O_2$ molarity in the precursor solution was 0.85 mM for one of the samples (referred to as Sample 48) and 1.7 mM for the other sample (referred to as Sample 49).

Rheological measurements of the hydrogel formation were performed with a HAAKE Rheoscope 1 rheometer (Karlsruhe, Germany) using a cone and plate geometry of 35 mm diameter and 0.945° cone angle. The measurements were taken at 37° C. in the dynamic oscillatory mode with a constant deformation of 1% and frequency of 1 Hz. To avoid slippage of samples during the measurement, a roughened glass bottom plate was used.

Selected contents and gelation parameters of the respective precursor solutions and the mechanical strength of Samples 48 and 49 are shown in Table X.

TABLE X

|  | Sample | |
| --- | --- | --- |
|  | Sample 48 | Sample 49 |
| Gtn-HPA (wt %) | 2 | 2 |
| HRP (units/ml) | 0.15 | 0.15 |
| $H_2O_2$ (mM) | 0.85 | 1.7 |
| G' (Pa) | 281 ± 19 | 841 ± 45 |
| Gel Point (s) | <30 | 45 ± 5 |
| Time for G' to reach plateau (s) | 78 ± 12 | 251 |

More specifically, the samples were prepared as follows.

Lyophilized Gtn-HPA conjugate was dissolved in PBS at a concentration of 2 wt %. Solutions of HRP and $H_2O_2$ with different concentrations were added sequentially to an aqueous solution of Gtn-HPA (2 wt %, 250 μl in PBS). 6 μl of HRP was added to 1 ml of Gtn-HPA solution to give a final HRP concentration of 0.15 units/ml. Crosslinking was initiated by adding 6 μl of a $H_2O_2$ solution with different concentrations to give final $H_2O_2$ concentration of 0.85 or 1.7 mM. Each solution was vortexed vigorously and then immediately applied to the bottom plate of the rheometer, by injecting the solution between two parallel glass plates clamped together with 1 mm spacing. The upper cone was then lowered to a measurement gap of 0.024 mm and a layer of silicon oil was carefully applied around the cone to prevent solvent evaporation during measurement. The crosslinking reaction was allowed to proceed for two hours. The sample hydrogels were slab-shaped.

For some tests, round hydrogel disks with diameters of 1.6 cm were cut out from the hydrogel slab using a circular mold. The hydrogel disks were swollen in PBS for 24 hours to reach swelling equilibrium and then sandwiched between plastic nets to facilitate retrieval of the hydrogels during degradation.

Figure 18:
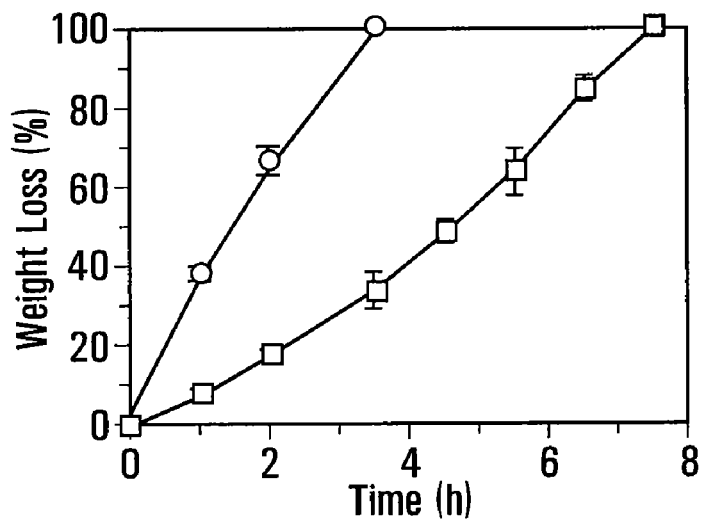
FIGS. 18, 19 and 20 are line diagrams showing cell growth in different sample hydrogels.

For degradation tests, the sample hydrogels were immersed in 20 ml of PBS containing 0.61 units/ml of type I collagenase and incubated at 37° C. in an orbital shaker at 100 rpm. The degree of degradation of the sample hydrogels was estimated by measuring the residual hydrogel weight. For measuring the residual weight, the sample hydrogels were removed from the solution, blotted dry and weighed at specific time points. Representative test results are shown in FIG. 18 for Samples 48 (circles) and 49 (squares). The data points represent average values with standard deviations. The results indicate that Sample 48 degraded much faster than Sample 49, confirming that the degradability of hydrogels can be controlled by selecting proper hydrogel stiffness.

For cell culturing, hMSCs were cultured in mesencult human basal medium supplemented with mesencult human supplement, and HFF-1 cells were grown in DMEM supplemented with 15% fetal bovine serum. hMSCs were used at a low passage number (p<6).

2D cell growth was attempted on the surface of the sample hydrogels. Human fibroblast (HFF-1) and hMSCs were respectively seeded on the surface of the sample hydrogels to evaluate cell attachment properties. Samples 48 and 49 both showed good cell attachment ability. The cell attachment was likely effected by the positively charged residues and RGD peptide sequences of Gtn. Both HFF-1 and hMSCs proliferated well on surfaces of Samples 48 and 49, but the cell growth rates were dependent on the stiffness of the particular sample hydrogel. In Samples 48 and 49, the rate of HFF-1 and hMSCs proliferation increased with the decrease of the hydrogel stiffness.

For 3D cell proliferation in the sample hydrogels, hMSC or HFF-1 were added to 1 ml of Gtn-HPA solution (2 wt %) in 6-well plate at final concentrations of $1 \times 10^5$ and $2 \times 10^5$ cells/ml, respectively. After the precursor solutions were prepared they were allowed to set for four hours before immersing the formed hydrogels in a culture medium. The culture medium was exchanged every 2-3 days. To evaluate the cell proliferation in hydrogels, the quantification of DNA was performed. The cell pellets were harvested by incubating the sample hydrogels with collagenase solution (6.7 unit/ml) for digestion of Samples 48 and 49. The cell pellets were lysed by a freeze-thaw cycle in 200 µl of DNA-free lysis buffer. The Samples were then incubated with 200 µl of PicoGreen working solution. Then, cell number in each solution was determined by the fluorescence measurement of the sample solution along with the known concentration of cell suspension for the standard curve. The fluorescence measurement was performed using a microplate reader with excitation and emission at 480 and 520 nm, respectively. For the observation of cell morphology in hydrogels, hydrogels containing cells were incubated with 2 µM of calcein acetoxymethyl ester for 1 h at 37° C. The morphology of fluorescently labeled cells was accessed using fluorescence microscope (Olympus 71, Japan).

Figure 19:
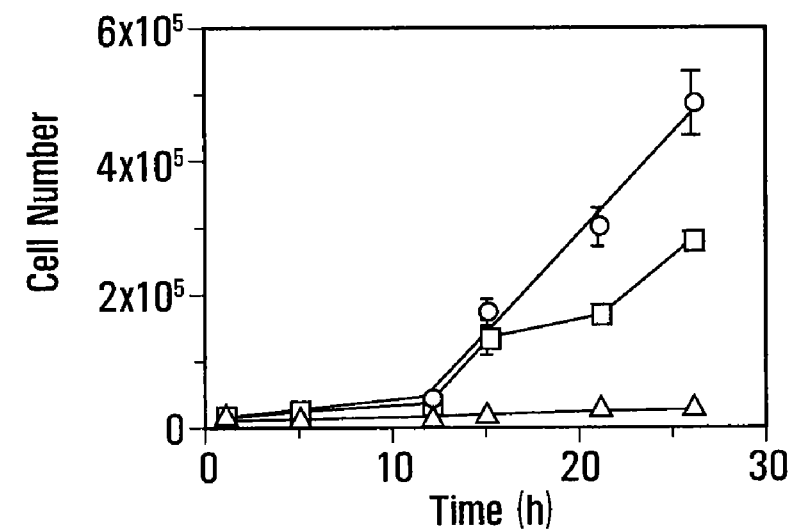
Figure 20:
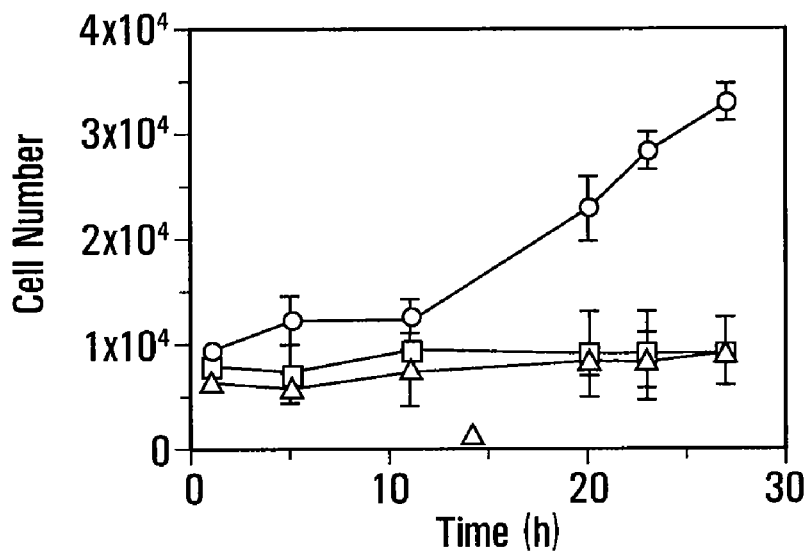

FIGS. 19 and 20 show representative results of 3D cell growth measurements obtained from Samples 48 (circles) and 49 (squares), and in a comparison sample of HA-phenol hydrogel (triangles). FIG. 19 shows results of hMSC proliferation, and FIG. 20 shows results of HFF-1 proliferation. The cells were grown in 3D within the sample hydrogels. 3D cell growth of both of HFF-1 and hMSCs was observed in Sample 48. In Sample 49, only HFF-1 growth was observed in 3D. A comparison sample hydrogel formed of a hyaluronic acid (HA)-phenol conjugate with G' value of 614 Pa was also tested for comparison purposes. No cell proliferation of either HFF-1 or hMSCs was observed in the comparison sample (HA hydrogels).

For hMSC differentiation tests, the cells were pre-treated with mitomycin C (10 µg/ml) for 2 h to inhibit the proliferation and washed three times with culture medium. The hydrogels containing mitomycin C treated hMSCs at final density of $1 \times 10^5$ cells/ml were prepared as described above. The culture was maintained for 3 weeks. For confocal imaging, the hydrogels were fixed with 4% formaldehyde solution at room temperature for 20 min. After washing, the cells were permeabilized using 0.5% Triton X-100 in PBS solution at room temperature for 5 min. The cells were then blocked in 0.05% Triton X-100 containing 1% bovine serum albumin at room temperature for 1 h. The samples were then incubated with the primary antibody in blocking buffer solution at 4° C. overnight. After washing, the cells were incubated with the fluorophore-conjugated secondary antibodies in the dark for 30 min. The cell nuclei were counterstained with DAPI (1:15, 000 in water of 5 mg/ml stock). Confocal images were taken with a confocal laser scanning microscopy (Olympus FV300, Japan). For western blotting, cells were harvested as described above. The cells in buffer (4% SDS, 20% glycerol and 0.02% bromophenol blue in Tris-HCl (0.125 M, pH 6.8)) were sonicated for 30 second. Cell lysate was boiled for 5 min, and was subjected to SDS-polyacrylamide gel electrophoresis. Proteins were transferred onto nitrocellulose, blocked, and labeled with HRP-conjugated secondary antibodies. Blot for β-actin was served as control to ensure constant protein loading level. All western blottings were performed in duplicate.

The percentage of HPA introduced to the amine groups of Gtn was determined by a conventional 2,4,6-trinitrobenzene sulfonic acid (TNBS) method. The result showed 90% of the amine group in Gtn was conjugated with HPA. The presence of Gtn-HPA conjugate was further confirmed by $^1$H NMR measurement. From the $^1$H NMR spectrum of Gtn-HPA, the peaks at chemical shift (δ) 6.8 ppm and 7.1 ppm indicated the presence of the aromatic protons of HPA, in addition to the aromatic protons of phenylalanine and tyrosine residues of Gtn (δ=7.3 ppm).

The formation of Gtn-HPA hydrogels was monitored using oscillatory rheometry to measure the storage modulus (G') against the shear strain. G' was used to indicate the stiffness of a given Sample. Values of G' were recorded to monitor when G' reached a plateau, which indicated that crosslinking had been completed. The test results showed that G' could be varied from a few hundred to a few thousands Pa by adjusting the $H_2O_2$ molarity in the precursor solutions with 2 wt % of Gtn-HPA conjugate. The gel point could be varied from about 1 s to 5 min by adjusting the HRP concentration in the precursor solution. It was found that in samples with G' higher than about 1000 Pa, cell proliferation in the samples were poor. As shown in Table X, G' increased with increased $H_2O_2$ molarity. The time needed for G' to reach a plateau also increased with increased $H_2O_2$ molarity. This result might indicate that HRP was continuously oxidized by $H_2O_2$ and reduced by HPA moieties, until all $H_2O_2$ had been depleted in the process of Gtn-HPA hydrogel forming. Thus, it was likely that a higher crosslinking density was achieved as a result of a higher amount of oxidized HPA, due to the higher molarity of $H_2O_2$.

The gel point of Samples 48 and 49 (with 0.15 units/ml of HRP) was less than 45 s. As such, Samples 48 and 49 should be suitable for use in an injection application.

The morphology of cells cultured in sample hydrogels were observed after 2 weeks of cell culture. The cells were stained by calcein acetoxymethyl ester (Calcein AM). HFF-1 and hMSC were allowed to grow inside the sample hydrogels. In the case of Samples 48 and 49, the HFF-1 spread out and interconnected in the sample hydrogels with filopodia-rich morphology. hMSCs were also proliferated well in Sample 48. However, the hMSC cells in sample 49 appeared to be much fewer, due to the stiffer environment. In contrast, both the HFF-1 and hMSCs in the comparison sample (HA-phenol hydrogel) appeared to be rounded over time, largely due to poor spreading of cells despite being of similar stiffness to the Gtn-HPA hydrogels. These results indicate that stiffness, degradability and cell adhesion property of the hydrogels may be adjusted to control cell proliferation in hydrogels.

In another test, hMSCs were pre-treated with mitomycin C to inhibit proliferation and were maintained inside samples 48 and 49 in a normal culture medium for three weeks. Mitomycin C had little impact on average cell shape and morphology. The cells were then immunostained with neuron-specific antibodies, neurofilament light chain, late neuronal marker neurofilament heavy chain (NFH), mid/late neuronal marker microtubule associated protein 2 (MAP2) and neuron-specific marker β3 tubulin. Neucli were counterstained with 4',6-diamidino-2-phenylindole (DAPI). In the obtained immunofluorescence images, it was found that cells in Sample 48 revealed expression of these neuron-specific proteins. In contrast, cells cultured on plastic culture plate or cells in the comparison sample (HA-phenol hydrogel) over the same period of culture did not express the neuron-specific proteins. It suggested that the catalysts $H_2O_2$ and HRP, which was present in the precursor solution, did not induce hMSCs differentiation, since both the HA-phenol and Gtn-HPA hydrogels were formed in a similar process using these catalysts.

It was found that, with a Western blots technique, hMSCs cultured inside Samples 48 and 49 for three weeks expressed protein markers for neuronal commitment, NFL, NFH, MAP2, and 33 tubulin, while cells cultured on plastic culture plate for the same period of time showed no neuronal protein marker expression. For cells harvested after two weeks of culture inside Samples 48 and 49, only 33 tubulin was detectable in western blots. Sample 48 expressed much more neuronal protein markers as compared to Sample 49.

To summarize, the stiffness of the samples hydrogels affected the cell proliferation rates; the rate of human fibroblast and hMSCs proliferation increased with the decrease of the hydrogel stiffness. The neurogenesis of hMSCs could also be controlled using hydrogel stiffness in a 3D context without the use of any additional biochemical signal.

Where a list of items is provided with an "or" before the last item herein, any one of the items in the list may be used; and a possible combination of any two or more of the listed items may also be used, as long as the combined items are not inherently incompatible, exclusive, or clearly unintended in the context.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method of forming a hydrogel, comprising:
   selecting an amount of horseradish peroxidase (HRP) and an amount of hydrogen peroxide ($H_2O_2$); and
   mixing a polymer comprising a crosslinkable phenol group, said amount of HRP and said amount of $H_2O_2$ in a solution, to crosslink said polymer to form said hydrogel,
   wherein said amount of HRP and said amount of $H_2O_2$ are selected to independently control a gelation rate in said solution and a crosslinking density in said hydrogel, with a constraint that the $H_2O_2$ molarity in said solution is within a pre-determined range and the HRP concentration in said solution is above a pre-determined threshold,
   said pre-determined range and threshold having been determined on the basis that, if said $H_2O_2$ molarity in said solution is limited to be within said range and said HRP concentration in said solution is limited to be above said threshold,
   said gelation rate in said solution would be substantially unaffected by variation in the selection of said $H_2O_2$ molarity within said range, and
   said crosslinking density in said hydrogel would be substantially unaffected by variation in the selection of said HRP concentration above said threshold.

2. The method of claim 1, wherein said $H_2O_2$ molarity is selected so that said hydrogel formed from said solution has a pre-selected storage modulus.

3. The method of claim 1, wherein said polymer comprises a conjugate of hyaluronic acid (HA) and tyramine (Tyr).

4. The method of claim 3, wherein said range has an upper limit of about 1 mM or less.

5. The method of claim 3, wherein said solution comprises from about 0.1 to about 20 w/v % of said conjugate of HA and Tyr.

6. The method of claim 1, wherein said polymer comprises a conjugate of a gelatin moiety and a phenol moiety.

7. The method of claim 6, wherein said gelatin moiety comprises gelatin and said phenol moiety comprises 3,4-hydroxyphenylpropionic acid (HPA).

8. The method of claim 7, wherein said conjugate has an average degree of phenol substitution of about 13.

9. The method of claim 8, wherein said phenol moiety further comprises tyramine.

10. The method of claim 9, wherein said conjugate has an average degree of phenol substitution of from about 16 to about 21.

11. The method of claim 6, wherein said hydrogel is for growing cells therein, and wherein said $H_2O_2$ molarity in said solution is selected to affect differentiation of said cells in said hydrogel.

12. The method of claim 11, wherein said cells comprise stem cells.

13. The method of claim 12, wherein said stem cells comprise human mesenchymal stem cells.

14. The method of claim 6, wherein said $H_2O_2$ molarity in said solution is selected to affect a growth rate of cells in said hydrogel.

15. The method of claim 6, wherein said conjugate is formed in a process comprising mixing HPA, N-Hydroxysuccinimide (NHS), and 1-ethyl-3(3-dimenthylaminopropyl)-carbodiimide hydrochloride (EDC-HCl) in a mixture to activate phenol groups of HPA; and adding gelatin to said mixture after activation of said phenol groups of HPA, to form a conjugate of gelatin and HPA.

16. The method of claim 15, wherein said process further comprising mixing tyramine, NHS, EDC-HCl, and said conjugate of gelatin and HPA in a mixture to form a conjugate of gelatin-HPA-tyramine.

17. The method of claim 1, wherein said solution further comprises a drug.

18. The method of claim 1, wherein said solution further comprises a protein.

19. The method of claim 1, wherein said solution further comprises cells.

20. The method of claim 1, comprising injecting said solution to a gelation site.

21. A method of forming hydrogels with different crosslinking densities from a polymer comprising a crosslinkable phenol group, comprising:
   mixing said polymer, horseradish peroxidase (HRP), and hydrogen peroxide ($H_2O_2$) in each one of a plurality of solutions, to crosslink said polymer in said each solution to form a respective hydrogel, wherein said solutions have a HRP concentration selected to achieve a pre-selected gelation rate and different $H_2O_2$ molarities selected to achieve different crosslinking densities in different hydrogels formed from respective solutions;

limiting said $H_2O_2$ molarities to be within a pre-determined range; and limiting said HRP concentration to be above a pre-determined threshold, wherein said pre-determined range and said pre-determined threshold are determined on the basis that, if said $H_2O_2$ molarities in said solutions are limited to be within said range and said HRP concentration in said solutions is limited to be above said threshold, gelation rates in said solutions would be substantially unaffected by variation in the selection of said $H_2O_2$ molarities within said range, and crosslinking densities in said hydrogels would be substantially unaffected by variation in the selection of said HRP concentration above said threshold.

22. The method of claim 21, wherein the $H_2O_2$ molarity in each solution is selected so that the respective hydrogel formed from said solution has a pre-selected storage modulus.

23. The method of claim 21, wherein said polymer comprises a conjugate of hyaluronic acid (HA) and tyramine (Tyr).

24. The method of claim 23, wherein said range has an upper limit of about 1 mM or less.

25. The method of claim 23, wherein said range is from about 0.146 to about 1.092 mM.

26. The method of claim 23, wherein said threshold is about 0.032 unit/ml.

27. The method of claim 23, wherein each one of said solutions comprises from about 0.1 to about 20 w/v % of said conjugate of HA and Tyr.

28. The method of claim 23, wherein said tyramine in said each solution has a molarity of from about 0.42 to about 21 mM.

29. The method of claim 21, wherein said polymer comprises a conjugate of a gelatin moiety and a phenol moiety.

30. The method of claim 29, wherein said gelatin moiety comprises gelatin and said phenol moiety comprises 3,4-hydroxyphenylpropionic acid (HPA).

31. The method of claim 30, wherein said conjugate has an average degree of phenol substitution of about 13.

32. The method of claim 30, wherein said phenol moiety further comprises tyramine.

33. The method of claim 29, wherein said $H_2O_2$ molarities in said solutions are selected to affect differentiation of cells in said hydrogels.

34. The method of claim 33, wherein said cells comprise stem cells.

35. The method of claim 34, wherein said stem cells comprise human mesenchymal stem cells.

36. The method of claim 26, wherein said $H_2O_2$ molarities in said solutions are selected to affect growth rates of cells in said hydrogels.

37. The method of claim 30, comprising mixing HPA, N-Hydroxysuccinimide (NHS), and 1-ethyl-3(3-dimenthylaminopropyl)-carbodiimide hydrochloride (EDC-HCl) to activate phenol groups of HPA;

adding gelatin to said mixture after activation of said phenol groups of HPA, to form a conjugate of gelatin and HPA.

38. The method of claim 32, further comprising mixing tyramine, NHS, EDC-HCl, and said conjugate of gelatin and HPA to form a conjugate of gelatin-HPA-tyramine.

* * * * *